(12) United States Patent
Dandler et al.

(10) Patent No.: US 11,998,670 B2
(45) Date of Patent: Jun. 4, 2024

(54) DISPOSABLE CARTRIDGE AND PUMP TRACK MECHANISM

(71) Applicant: DIALITY INC., Irvine, CA (US)

(72) Inventors: Andres Dandler, Irvine, CA (US); Clayton Poppe, Irvine, CA (US); Miroslav Mitrovic, Irvine, CA (US)

(73) Assignee: DIALITY INC., Irvine, CA (US)

( * ) Notice: Subject to any disclaimer, the term of this patent is extended or adjusted under 35 U.S.C. 154(b) by 883 days.

(21) Appl. No.: 17/088,437

(22) Filed: Nov. 3, 2020

(65) Prior Publication Data

US 2021/0128808 A1    May 6, 2021

Related U.S. Application Data

(60) Provisional application No. 62/930,780, filed on Nov. 5, 2019.

(51) Int. Cl.
*A61M 1/16*    (2006.01)
*A61M 1/14*    (2006.01)
(Continued)

(52) U.S. Cl.
CPC ............ *A61M 1/155* (2022.05); *A61M 1/152* (2022.05); *A61M 1/1524* (2022.05);
(Continued)

(58) Field of Classification Search
CPC .. A61M 1/152; A61M 1/1522; A61M 1/1524; A61M 1/154; A61M 1/155; A61M 1/156; A61M 1/16; A61M 1/1621; A61M 1/262; A61M 1/36222; A61M 1/362227; A61M 1/36225; A61M 60/109;
(Continued)

(56) References Cited

U.S. PATENT DOCUMENTS 3,864,259 A    2/1975    Newhart
4,617,115 A    10/1986    Vantard
(Continued)

FOREIGN PATENT DOCUMENTS

CN    110420362 A1    11/2019
EP    3666310 A1    6/2020
(Continued)

OTHER PUBLICATIONS

WO, PCT/US20/58731 ISR and Written Opinion, dated Dec. 8, 2022.
EP, EP 20884874.7 Extended European Search Report, dated Nov. 6, 2023.

*Primary Examiner* — John Kim
(74) *Attorney, Agent, or Firm* — One LLP; David G. Duckworth

(57) ABSTRACT

Disclosed are example embodiments of a dialysis machine having a frame, a cartridge cassette, one or more alignment-locking features, and an actuation mechanism. The frame is fixedly coupled to the dialysis machine, and the cassette is slidably coupled to the frame. The cassette can have one or more track structures, with each of the one or more track structures having a rotor and one or more rollers. The one or more alignment-locking features extend from the frame and are configured to be inserted into one or more alignment features of a disposable cartridge that functions to secure or release the disposable cartridge. The actuation mechanism is made to slide the cassette with respect to the one or more track structures.

18 Claims, 23 Drawing Sheets

(51) Int. Cl.
  *A61M 1/26* (2006.01)
  *A61M 1/36* (2006.01)
  *A61M 60/109* (2021.01)
  *A61M 60/279* (2021.01)
  *A61M 60/37* (2021.01)
  *A61M 60/438* (2021.01)
  *A61M 60/835* (2021.01)
  *A61M 60/847* (2021.01)

(52) U.S. Cl.
  CPC .............. *A61M 1/156* (2022.05); *A61M 1/16* (2013.01); *A61M 1/1621* (2014.02); *A61M 1/262* (2014.02); *A61M 1/36222* (2022.05); *A61M 1/362227* (2022.05); *A61M 1/36225* (2022.05); *A61M 60/109* (2021.01); *A61M 60/279* (2021.01); *A61M 60/37* (2021.01); *A61M 60/438* (2021.01); *A61M 60/835* (2021.01); *A61M 60/847* (2021.01); *A61M 1/1522* (2022.05); *A61M 1/154* (2022.05); *A61M 2205/12* (2013.01); *A61M 2205/121* (2013.01); *A61M 2205/127* (2013.01); *A61M 2205/332* (2013.01); *A61M 2205/702* (2013.01)

(58) Field of Classification Search
  CPC .. A61M 60/279; A61M 60/37; A61M 60/438; A61M 60/835; A61M 60/847; A61M 2205/12; A61M 2205/121; A61M 2205/127; A61M 2205/332; A61M 2205/702; A61M 2205/58
  See application file for complete search history.

(56) References Cited

U.S. PATENT DOCUMENTS

| | | | |
|---|---|---|---|
| 4,661,246 A | 4/1987 | Ash | |
| 5,139,637 A | 8/1992 | MacConnell | |
| 6,695,806 B2 | 2/2004 | Gelfand | |
| 6,821,432 B2 | 11/2004 | Metzner | |
| D606,197 S | 12/2009 | Collins | |
| 7,967,022 B2 | 6/2011 | Grant | |
| 8,042,563 B2 | 10/2011 | Wilt | |
| 8,273,049 B2 | 9/2012 | Demers | |
| 8,298,167 B2 | 10/2012 | Peters | |
| 8,317,492 B2 | 11/2012 | Gemers | |
| 8,400,298 B2 | 3/2013 | Rada | |
| 8,459,292 B2 | 6/2013 | Wilt | |
| 8,499,780 B2 | 8/2013 | Wilt | |
| 8,888,470 B2 | 11/2014 | Demers | |
| 8,926,294 B2 | 1/2015 | Demers | |
| 8,985,133 B2 | 3/2015 | Grant | |
| 8,992,189 B2 | 3/2015 | Wilt | |
| 9,039,395 B2 | 5/2015 | Gray | |
| 9,272,082 B2 | 3/2016 | Demers | |
| 9,358,332 B2 | 6/2016 | McGill | |
| 9,364,599 B2 | 6/2016 | Giordano | |
| 9,488,167 B2 | 11/2016 | Gray | |
| 9,550,018 B2 | 1/2017 | Demers | |
| 9,593,678 B2 | 3/2017 | Gray | |
| 9,649,418 B2 | 5/2017 | Demers | |
| 9,677,554 B2 | 6/2017 | Wilt | |
| 9,700,660 B2 | 7/2017 | Demers | |
| 9,951,768 B2 | 4/2018 | Grant | |
| 10,022,673 B2 | 7/2018 | Fulkerson | |
| 10,077,766 B2 | 9/2018 | Demers | |
| 10,265,451 B2 | 4/2019 | McGill | |
| 10,451,572 B2 | 10/2019 | Jones | |
| 2004/0127840 A1 | 7/2004 | Gara et al. | |
| 2004/0158189 A1 | 8/2004 | Tonelli et al. | |
| 2008/0132828 A1 | 6/2008 | Howard | |
| 2011/0163023 A1 | 7/2011 | Kreusch et al. | |
| 2014/0012201 A1 | 1/2014 | Schaefer | |
| 2018/0214620 A1 | 8/2018 | Childers et al. | |

FOREIGN PATENT DOCUMENTS

| | | |
|---|---|---|
| GB | 2110564 A | 6/1983 |
| WO | 2020053442 | 3/2020 |

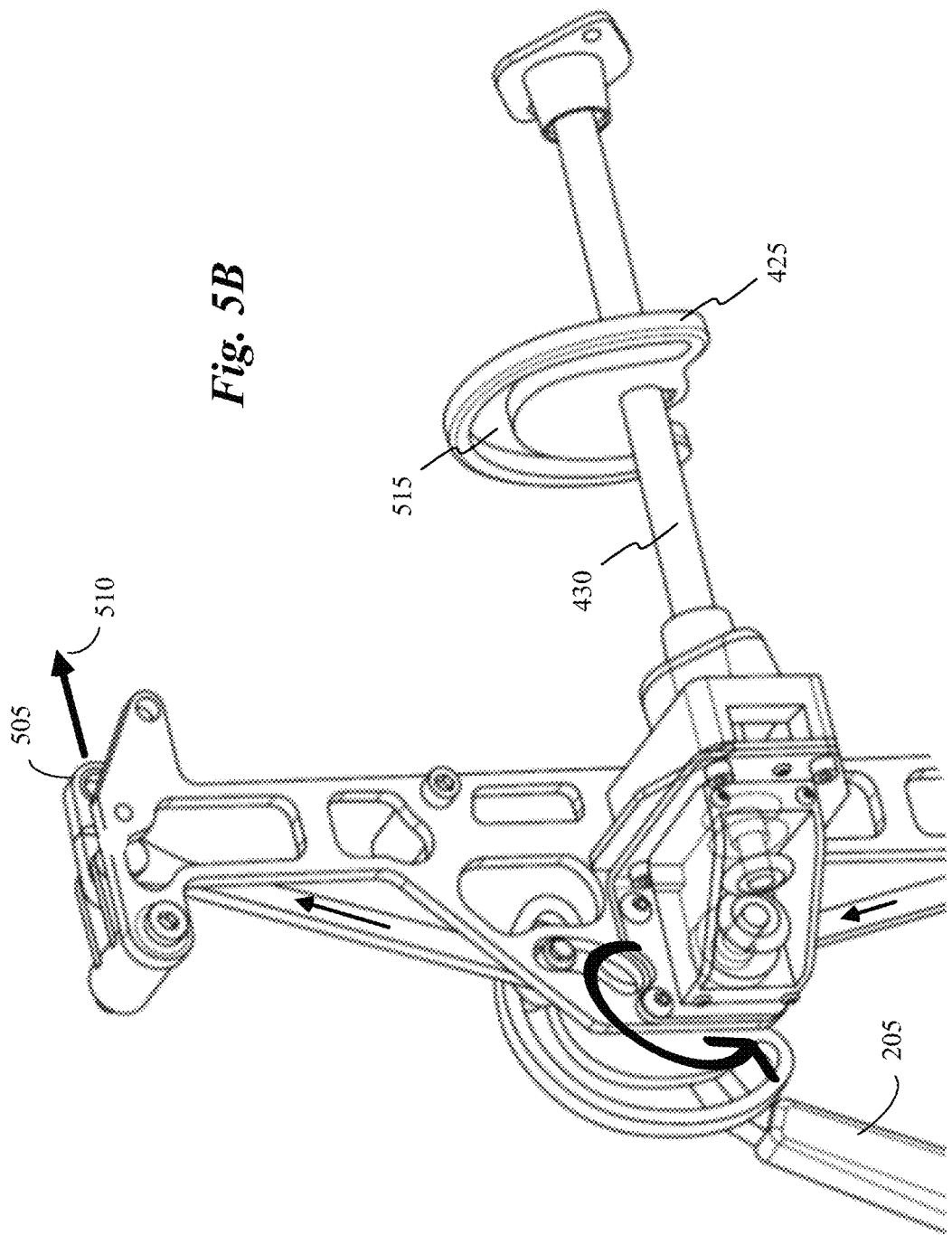

DISPOSABLE CARTRIDGE AND PUMP TRACK MECHANISM

CROSS-REFERENCE TO RELATED APPLICATIONS

This application claims priority to and benefit of U.S. Provisional Application No. 62/930,780 entitled "DISPOSABLE CARTRIDGE AND PUMP TRACK MECHANISM", filed Nov. 5, 2019, which is incorporated herein by reference in its entirety for all purposes.

FIELD

The claimed invention relates to an artificial kidney system for use in providing dialysis. In some embodiments, the present disclosure is directed to a hemodialysis system having an actuatable platform to enable easy installation of the disposable cartridge.

BACKGROUND

Hemodialysis is a medical procedure that is used to achieve the extracorporeal removal of waste products including creatine, urea, and free water from a patient's blood involving the diffusion of solutes across a semipermeable membrane. Failure to properly remove these waste products can result in renal failure.

During hemodialysis, the patient's blood is removed by an arterial line, treated by a dialysis machine, and returned to the body by a venous line. The dialysis machine includes a dialyzer containing a large number of hollow fibers forming a semipermeable membrane through which the blood is transported. In addition, the dialysis machine utilizes a dialysate liquid, containing the proper amounts of electrolytes and other essential constituents (such as glucose), that is also pumped through the dialyzer.

Typically, dialysate is prepared by mixing water with appropriate proportions of an acid concentrate and a bicarbonate concentrate. Preferably, the acid and the bicarbonate concentrate are separated until the final mixing right before use in the dialyzer as the calcium and magnesium in the acid concentrate will precipitate out when in contact with the high bicarbonate level in the bicarbonate concentrate. The dialysate may also include appropriate levels of sodium, potassium, chloride, and glucose.

The dialysis process across the membrane is achieved by a combination of diffusion and convection. The diffusion entails the migration of molecules by random motion from regions of high concentration to regions of low concentration. Meanwhile, convection entails the movement of solute typically in response to a difference in hydrostatic pressure. The fibers forming the semipermeable membrane separate the blood plasma from the dialysate and provide a large surface area for diffusion to take place which allows waste, including urea, potassium and phosphate, to permeate into the dialysate while preventing the transfer of larger molecules such as blood cells, polypeptides, and certain proteins into the dialysate.

Typically, the dialysate flows in the opposite direction to blood flow in the extracorporeal circuit. The countercurrent flow maintains the concentration gradient across the semipermeable membrane so as to increase the efficiency of the dialysis. In some instances, hemodialysis may provide for fluid removal, also referred to as ultrafiltration. Ultrafiltration is commonly accomplished by lowering the hydrostatic pressure of the dialysate compartment of a dialyzer, thus allowing water containing dissolved solutes including electrolytes and other permeable substances to move across the membrane from the blood plasma to the dialysate. In rarer circumstances, fluid in the dialysate flow path portion of the dialyzer is higher than the blood flow portion, causing fluid to move from the dialysate flow path to the blood flow path. This is commonly referred to as reverse ultrafiltration. Since ultrafiltration and reverse ultrafiltration can increase the risks to a patient, ultrafiltration and reverse ultrafiltration are typically conducted only while supervised by highly trained medical personnel.

Unfortunately, hemodialysis suffers from numerous drawbacks. An arteriovenous fistula is the most commonly recognized access point. To create a fistula, a doctor joins an artery and a vein together. Since this process bypasses the patient's capillaries, blood flows rapidly. For each dialysis session, the fistula must be punctured with large needles to deliver blood into, and then return blood from the dialyzer. Typically, this procedure is done three times a week and for 3-4 hours per each treatment. To a lesser extent, patients conduct hemodialysis at home. Home hemodialysis is typically done for two hours, six days a week. Home hemodialysis is considered less stressful and is considered more simplistic as typically conducted with catheters. However, home hemodialysis requires more frequent treatment.

Home hemodialysis suffers from still additional disadvantages. Current home hemodialysis systems are big, complicated, intimidating and difficult to operate. The equipment requires significant training. Home hemodialysis systems are currently too large so as to be portable, thereby preventing hemodialysis patients from traveling. Home hemodialysis systems are expensive and require a high initial monetary investment, particularly compared to in-center hemodialysis where patients are not required to pay for the machinery. Present home hemodialysis systems do not adequately provide for the reuse of supplies, making home hemodialysis economically less feasible to medical suppliers. Because of the above-mentioned disadvantages, very few motivated patients undertake the drudgery of home hemodialysis.

Accordingly, there is a significant need for a hemodialysis system that is transportable, light weight, easy to use, patient friendly and thus capable of in-home use.

SUMMARY

Disclosed herein are examples of a dialysis systems. In one example, a dialysis system includes a disposable cartridge with a housing, and a first, a second, and a third set of tubing line mounted on the housing. Each set of tubing lines has a U-shape section designed to fall into the recessed track of the dialysis machine. The housing can have two or more alignment features, which are designed to receive an alignment-locking feature from the dialysis system. The alignment-locking feature is designed to pull the housing of cartridge into the cavity of the dialysis machine. This action secures the housing to the frame of the dialysis machine.

The two or more alignment features can be a slot, a hole, a cylindrical feature that reside on the dialysis machine. The alignment-locking feature can be a pin having actuatable side fingers, which are designed to extend outward to grab onto the housing of the disposable cartridge when the pin is pulled away from the housing. The actuatable side fingers of the pin are also designed to fold inward when the pin is pushed forward toward the housing.

In some embodiments, the dialysis system also includes: an actuation mechanism; a cassette having the recessed track to receive the first second and third sets of tubing line. The cassette can be slidably attached to the cartridge cavity or the frame of the dialysis machine. When actuated, the actuation mechanism is designed to slide the cassette to engage or disengage the tubing lines. In some embodiments, the actuation mechanism is designed to slide the cassette inward and push the sets of tubing line against the roller, when set to a lock state.

The actuation mechanism is also designed to slide the cassette outward to release pressure on the sets of tubing lines when set to an open state. In some embodiments, the actuation mechanism is designed to push the pin forward and retract the side fingers when set to a lock state.

When set to an open state, the actuation mechanism is designed to pull the pin backward and expand the side fingers. In some embodiments, the actuation mechanism includes a lever coupled to a first shaft, a first cam coupled to the first shaft, a plurality of linkages coupled to the first cam, and a sliding element coupled to the plurality of linkages and to the cassette. The plurality of linkages are arranged such the cassette is slid inward or outward when the lever is actuated.

The actuation mechanism further includes: a gear assembly coupled to the first shaft; a second shaft coupled to the gear assembly; a second cam coupled to the second shaft; and a pull plate coupled to the second cam and to the pin (e.g., alignment-locking feature). The pull plate and the pin are concurrently actuated forward or backward when the lever is actuated.

The dialysis machine can include: a frame fixedly coupled to the dialysis machine and a cassette slidably coupled to the frame. The cassette can include one or more track structures, with each of the one or more track structures having a rotor and one or more rollers. The dialysis machine also includes one or more alignment-locking features extending from the frame and an actuation mechanism. The one or more alignment-locking features are designed to be inserted into one or more alignment features of a disposable cartridge. Once inserted, the alignment-locking features can secure or release the disposable cartridge.

The actuation mechanism is made to slide the cassette with respect to the one or more track structures and to actuate the one or more alignment-locking features to either secure or release the disposable cartridge. The actuation mechanism can include a linkage assembly designed and fabricated to translate the cassette while the frame remains stationary and to actuate the one or more alignment-locking features to lock or release the disposable cartridge. The linkage assembly is designed to slide the cassette inward and push the sets of tubing line against the roller and the internal wall of the recessed track when the linkage assembly is set to a close state. The linkage assembly is also designed to slide the cassette outward to release pressure on the sets of tubing lines when the linkage assembly is set to an open state.

The linkage assembly is designed (and made) to push the pin forward and retract the side fingers when set to a lock state. The linkage assembly is also designed to pull the pin backward and expand the side fingers when it is set to an open state. The linkage assembly can also include: a lever coupled to a first shaft a first cam coupled to the first shaft; a plurality of linkages coupled to the first cam; and a sliding element coupled to the plurality of linkages and to the cassette. The plurality of linkages can be arranged such the cassette is slid inward or outward when the lever is actuated.

In some embodiments, the linkage assembly further includes: a gear assembly coupled to the first shaft; a second shaft coupled to the gear assembly; a second cam coupled o the second shaft; and a pull plate coupled to the second cam and to the pin wherein the pull plate and the pin are concurrently actuated forward or backward when the lever is actuated. The dialysis machine also includes a disposable cartridge that has a housing, which can have one or more alignment features designed to receive one or more alignment locking features from the frame of the dialysis machine. The dialysis machine also includes a first, a second, and a third set of tubing line coupled on the housing. Each set of tubing lines can have a U-shape section designed to fall into the one or more track structures of the cassette.

In some embodiments, the actuation mechanism can be a collection of one or more motors configured to: translate the cassette with respect to the frame and to advance or retract the pull-pin in order to release or capture the disposable cartridge. The collection of one or more motors can be coupled to a controller, which is configured to control the actuation of the cassette and a plurality of pull-pins The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes and may not have been selected to delineate or circumscribe the disclosed subject matter.

BRIEF DESCRIPTION OF THE DRAWINGS

The foregoing summary, as well as the following detailed description, is better understood when read in conjunction with the accompanying drawings. The accompanying drawings, which are incorporated herein and form part of the specification, illustrate a plurality of embodiments and, together with the description, further serve to explain the principals involved and to enable a person skilled in the relevant art(s) to make and use the disclosed technologies.

FIGS. 5A and 5B are perspective views of an actuation mechanism in accordance with some embodiments of the present disclosure.

The figures and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures to indicate similar or like functionality.

DETAILED DESCRIPTION

Disposable Cartridge

The disposable cartridge is one of the most important pieces of a dialysis system as it contains the fluid pathways in direct contact with the patient's blood. For this reason, the pathway has to be clean and free from foreign materials. The disposable has to be tightly coupled to the machine so that the sensors and actuators can interface with the disposable in a reliable fashion. Finally, the disposable is one of the main drivers of the cost of treatment and therefore has to be inexpensive.

Figure 1A:
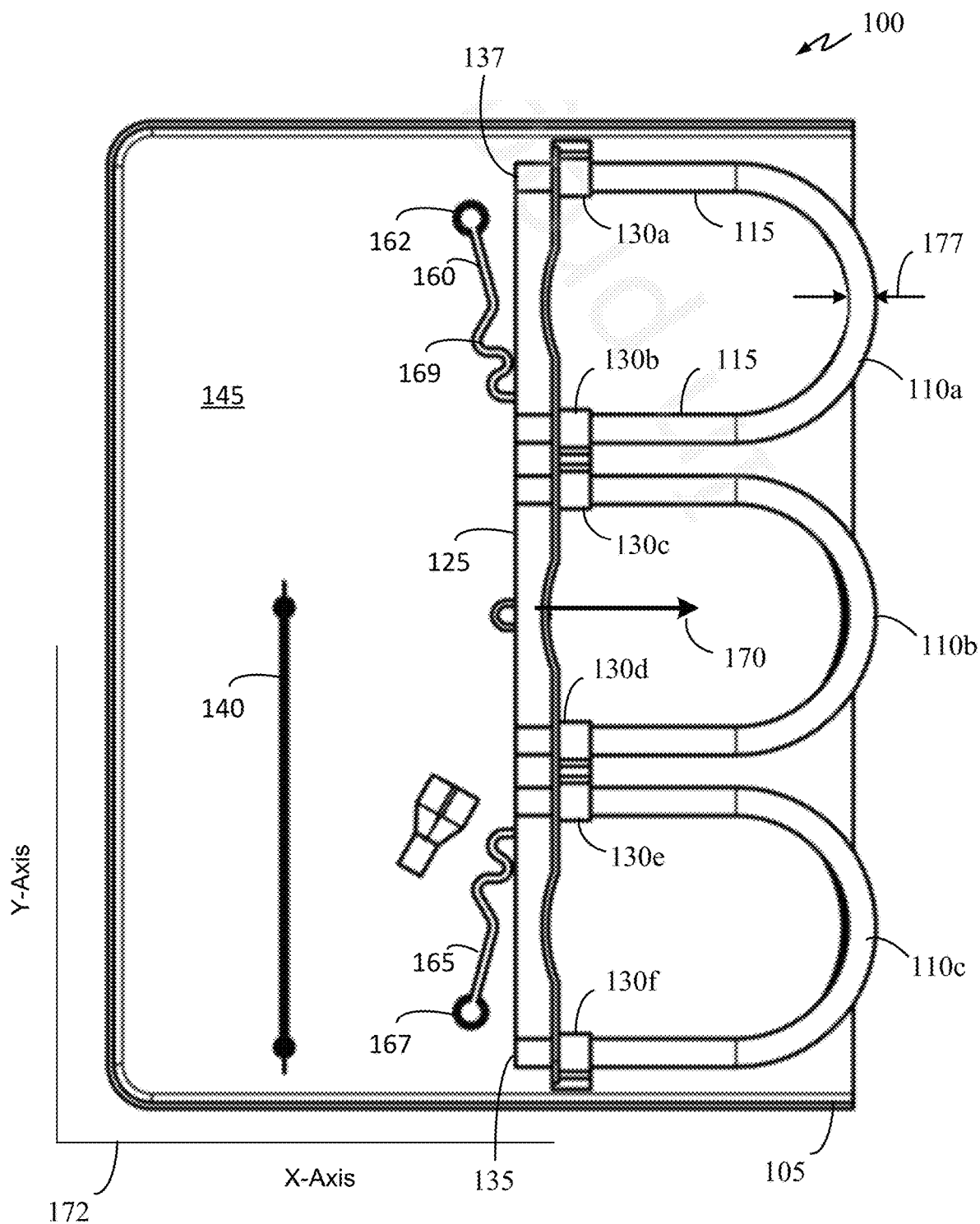
FIG. 1A is a side view of a disposable cartridge in accordance with some embodiments of the present disclosure.
Figure 1B:
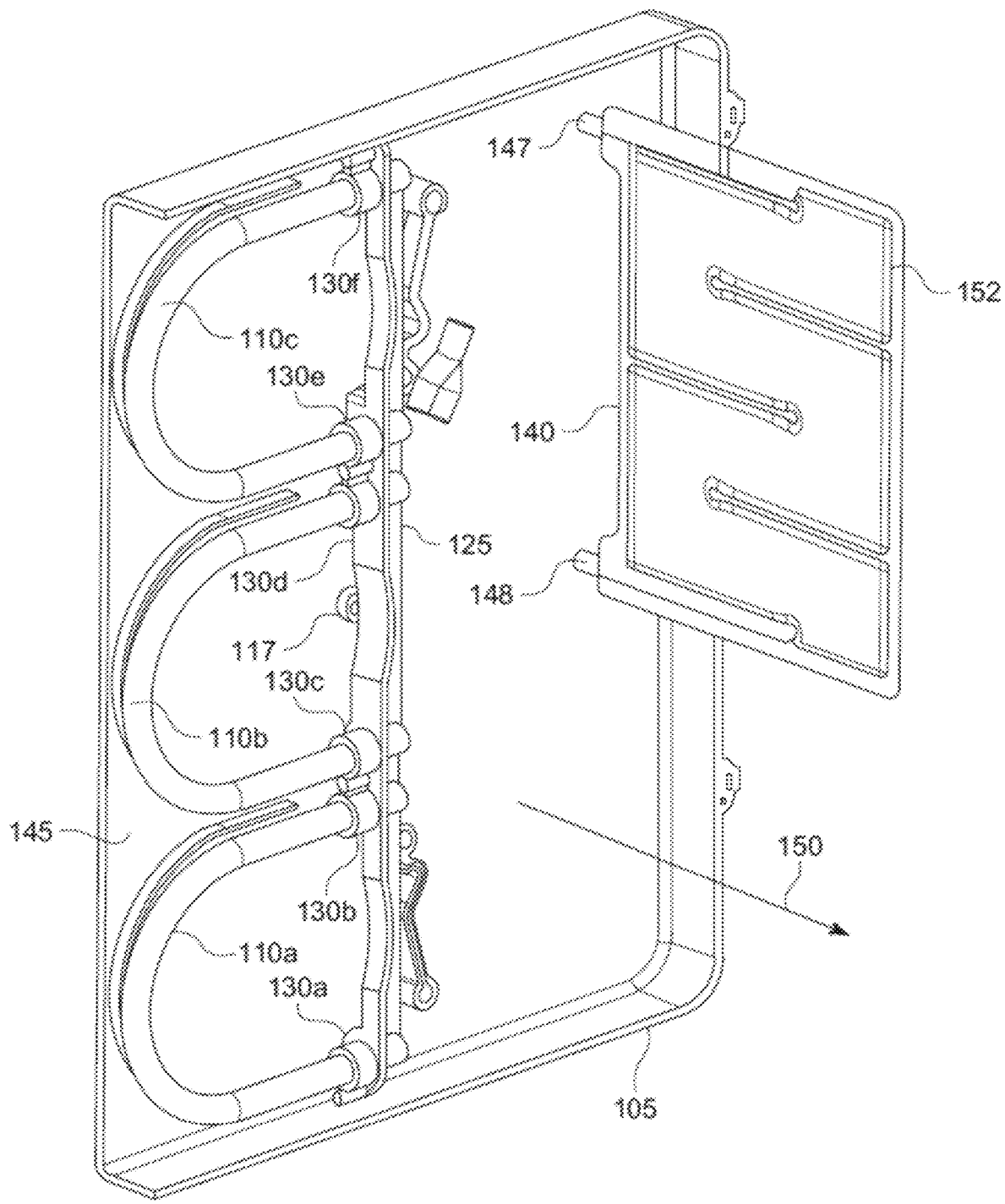
FIG. 1B is a perspective view of the disposable cartridge of FIG. 1A in accordance with some embodiments of the present disclosure.

FIGS. 1A and 1B illustrate a disposable cartridge 100 in accordance with some embodiments of the present disclosure. FIG. 1A is a top view of disposable cartridge 100, and FIG. 1B is a perspective view of disposable cartridge 100, both of which will be discussed concurrently. Disposable cartridge 100 can include a housing 105, a tubing-support structure 125, floating suspension structures 160 and 165, and tubing lines 110a, 110b, and 110c. Housing 105 can be made from inexpensive and recyclable materials such as plastics. Housing 105 can include a plurality of alignment features (not shown) configured to assist the alignment of housing 105 onto the body of the dialysis machine. Housing 105 can also include a plurality of alignment features 117 to assist the alignment of tubing-support structure 125 onto housing 105. Tubing-support structure 125 can have a plurality of built-in couplings 130a through 130f configured to receive and tightly hold openings of tubing lines 110a, 110b, and 110c in place while allow fluid to pass therethrough.

Tubing lines 110 (i.e., 110a, 110b, 110c) can have a predetermined pathway having an overall shape such as, but not limited, a U shape. The pathway of tubing lines 110 can have other shape such a half circle, for example.

Disposable cartridge 100 can have one or more tubing lines (i.e., 110a, 110b, 110c) which may carry blood from the patient's artery, blood to a patient's vein, dialysate to the dialyzer, or dialysate from the dialyzer. For example, disposable cartridge 100 can have two tubing lines 110a and 110b. In another example, disposable cartridge 100 can have four tubing lines. As shown, disposable cartridge 100 has three tubing lines that are coupled on tubing-supporting structure 125 by couplings 130a through 130f. Each tubing line is secured and held in place by two couplings. Tubing lines 110 can be made of medical grade PVC or other flexible materials such as rubber.

In some embodiments, coupling 130a can receive blood from an arterial blood line and coupling 130f can be directly or indirectly coupled to a venous blood line. The fluid pathway can also be reversed. For example, coupling 130f can receive blood from an arterial blood line and coupling 130a can be directly or indirectly coupled to a venous blood line. In some embodiments, instead of blood, dialysate can be fed into one or more of tubing lines 110a, 110b, and 110c. Dialysate can also be fed into heating bag 140 instead of a patient's blood. If dialysate is used in one of these pathways, then one skilled in the art would understand to add additional tubing lines in order properly route the dialysate and the blood from one of the other pathways to a dialyzer (not shown).

In some embodiments, disposable cartridge 100 can include one or more additional tubing lines (not shown) that connect coupling pairs 130b-130c and 130d-130e. Disposable cartridge 100 can also include an additional tubing line (not shown) that directly or indirectly connects an outlet 135 at coupling 130f to an inlet (not shown) of heater bag 140. Alternatively, outlet 137 at coupling 130a can be coupled to the inlet of heater bag 140 using additional tubing line (not shown). Although not shown, there can be one or more intermediate parts (e.g., valves, couplings, pumps, dialyzer, tubing lines) between outlet 135 and the inlet of heating bag 140. For example, there can be a tubing line that runs from outlet 130f to opposite side of main surface 145 of housing 105 and back into inlet 147 of heating bag 140. Main surface 145 is the surface of housing 105 that is facing tubing lines 110, in the direction 150 (see FIG. 1B).

Referring to FIG. 1B, disposable cartridge 100 can optionally include heating bag 140, which can be hingedly mounted (hinges not shown) to the main surface 145 of housing 105. This enables heating bag 140 the ability of lying flat against the main surface 145 and swinging perpendicular to the main surface (parallel to direction 150), as illustrated in FIG. 1B. Heating bag 140 can be secured to main surface 145 at two or more locations, which can also be couplings formed onto main surface 145. Heating bag 140 includes inlet coupling 147 and outlet coupling 148, both of which can also function as anchors for supporting and anchoring heating bag 140 onto main surface 145.

Heating bag 140 can include an internal channel having a pattern 152. The internal channel is designed to provide a large surface area for which blood can flow and be easily heated by the large surface area of the channel When disposable cartridge 100 is installed onto the dialysis machine, cartridge 100 is inserted onto the dialysis machine in the direction 150, which is normal to main surface 145. As disposable cartridge 100 is being installed, heating bag 140 is inserted into a slot on the dialysis machine. The slot can include one or more heating elements that provide heat to heating bag 140, which can have an outer layer made from a heat conductive material (e.g., aluminum, copper). Pattern 152 can have a continuous 'S' pattern as shown. Alternatively, pattern 152 can have a circular, zigzag, or spiraling pattern.

In some embodiments, heating bag 140 can include its own heating elements disposed on the outer surface of heating bag 140. However, since cartridge 100 is a disposable cartridge, the heating elements can be disposed on the dialysis machine and heating bag 140 can be made of inexpensive materials such as polyvinyl chloride (PVC) or other medical grade plastics.

Couplings 147 and 148 can be a pivotable couplings such that heating bag 140 can be folded substantially parallel to main surface 145 during transport or while being packaged. Alternatively, heating bag 140 can be secured coupled to couplings 147 and 148 during the installation process of disposable cartridge 100.

Referring back to FIG. 1A, tubing-support structure 125 can include to spring member 160 and 165. Spring member 160 can be pivotably attached to pivot point 162, and spring member 165 can be pivotably attached to pivot point 167. Each spring member can be made from plastic, metal, or other suitable materials. In some embodiments, spring members 160 and 165 are made from the same material as tubing-support structure 125, which can be molded, machined or 3D printed with high accuracy using a medical grade (FDA approved) plastic. In other words, tubing-support structure 125 and spring members 160 and 165 can be a single integrated unit. Spring members 160 and 165 can be designed to have a natural spring constant (e.g., k constant) such that tubing-support structure 125 is constantly pushed toward the direction 170, which is parallel to main surface 145 of housing 105.

Each of spring members 160 and 165 is designed to have certain geometric features 169 (e.g., bends, twists) to impart a spring like force in the direction 170. By varying the geometric features 169, spring members 160 and 165 can be designed to impart a predetermined amount force on tubing-structure 125 toward direction 170.

In some embodiments, tubing-support structure 125 is mounted to housing 105 at two locations, attachment points 162 and 167. This enables tubing-support structure 125 to float within housing 105. This unique design gives tubing-support structure 125 some room to move along the x-axis 172 while restricting movement in the z-axis (perpendicular to main surface 145). In some embodiments, the locations of attachment points 162 and 167 and the k-constant of spring members 160 and 165 are configured such that tubing-support structure can move at least the width 177 of tubing line 110*a*. In this way, during the installation of disposable cartridge 100, tubing lines 110 can easily be moved if necessary, such that they are properly seated into a pump track (not shown), which will be discussed below.

In some embodiments, attachment points 162 and 167 can be a pivotable point. In other words, spring member 160 can be pivotably attached to attachment point 162. Similarly, spring member 165 can be pivotably attached to attachment point 167. Spring members 162 and 167 can be shaped such that only movement along the x-axis is allowed and movement along the z-axis (out or into the paper) is inhibited. This can be done by making the spring member thicker along the z-axis. Movement along the y-axis can be restricted by attachment points 162 and 167 and/or by a sidewall of housing 105.

Figure 1D:
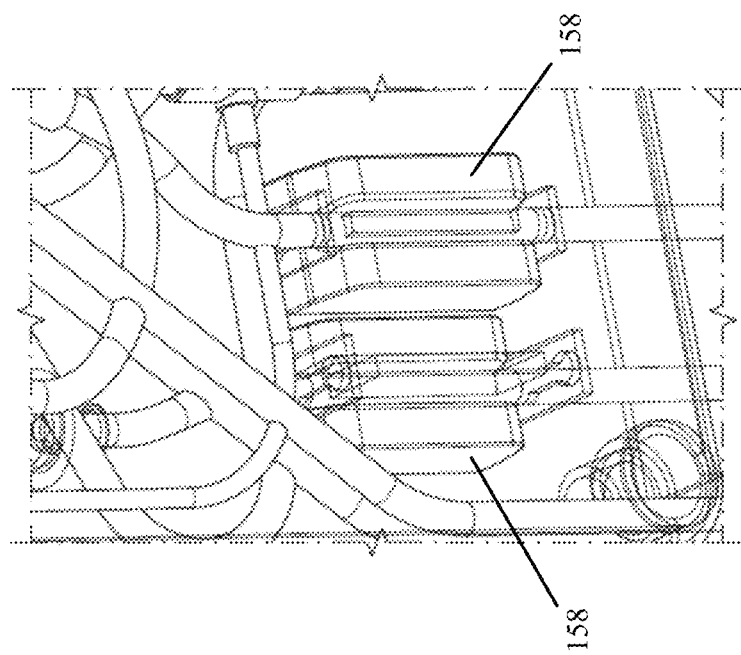
FIG. 1D is a perspective view of the sensors in FIG. 1C on a dialysis machine in accordance with some embodiments of the present disclosure.
Figure 1C:
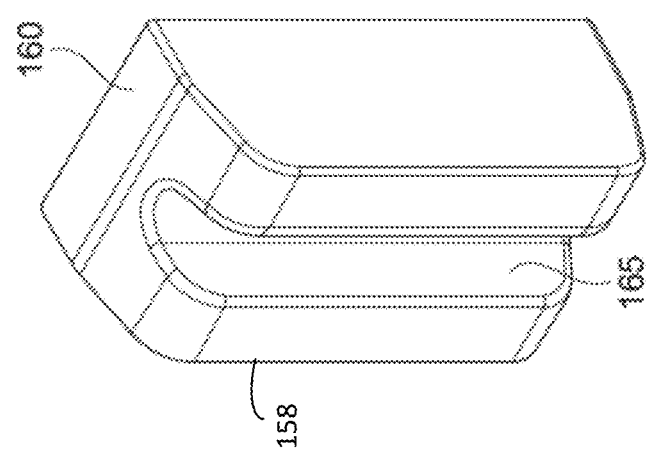
FIG. 1C is a perspective view of one of the sensors in accordance with some embodiments of the present disclosure.

FIG. 1C illustrates a sensor 158 in accordance with some embodiments of the present disclosure. FIG. 1D illustrates how tubing lines can be engaged with sensor 158, which can be mounted on a frame or body of the dialysis machine. Sensor 158 can be mounted on a portion of the dialysis machine such that when disposable cartridge 100 is installed, one of the tubing lines would automatically be guided into slot 165 of sensor 160 (see FIG. 1D).

Sensor 158 is configured to sense pressure through a tubing line, which can be guided and held using one or more alignment features (not shown) on housing 105. The disclosed dialysis machine (not shown) can include one or more sensors disposed.

Sensor can include channel (e.g., slot) 165, which can be a V-shape or U-shape channel In some embodiments, channel 165 has a V-shape near the bottom. Channel 165 includes a sensor 160 at the bottom that is configured to detect the expansion pressure exerted by the outer surface of tubing line when pressure inside the tubing line pushes outward. For example, when a tubing line is inserted into sensor 158, the tubing line would exert a force on sensor 160 at the bottom of channel 165. This initial force can also indicate that the tubing has been properly placed in the sensor. In some embodiments, after disposable cartridge 100 is installed, if the initial force is not detected or does not have a predetermined range, an alarm can be activated to indicate an error in the installation of disposable cartridge 100. Once disposable cartridge 100 and tubing lines are properly installed into the dialysis machine, the control system (not shown) of the dialysis machine can begin a warmup cycle to heat up and relax the tubing lines.

The control system can also bring the pressure inside the tubing to atmospheric pressure. Additionally, the control system can adjust the sensor offset reading in order to read ambient pressure. From that point, the control system can monitor the sensor to determine if a tubing occlusion or very high pressure is present by converting the force of the tubing on the sensor to a pressure inside the tubing. If an occlusion is detected, the control system can activate an alarm to warn the user.

Figure 1E:
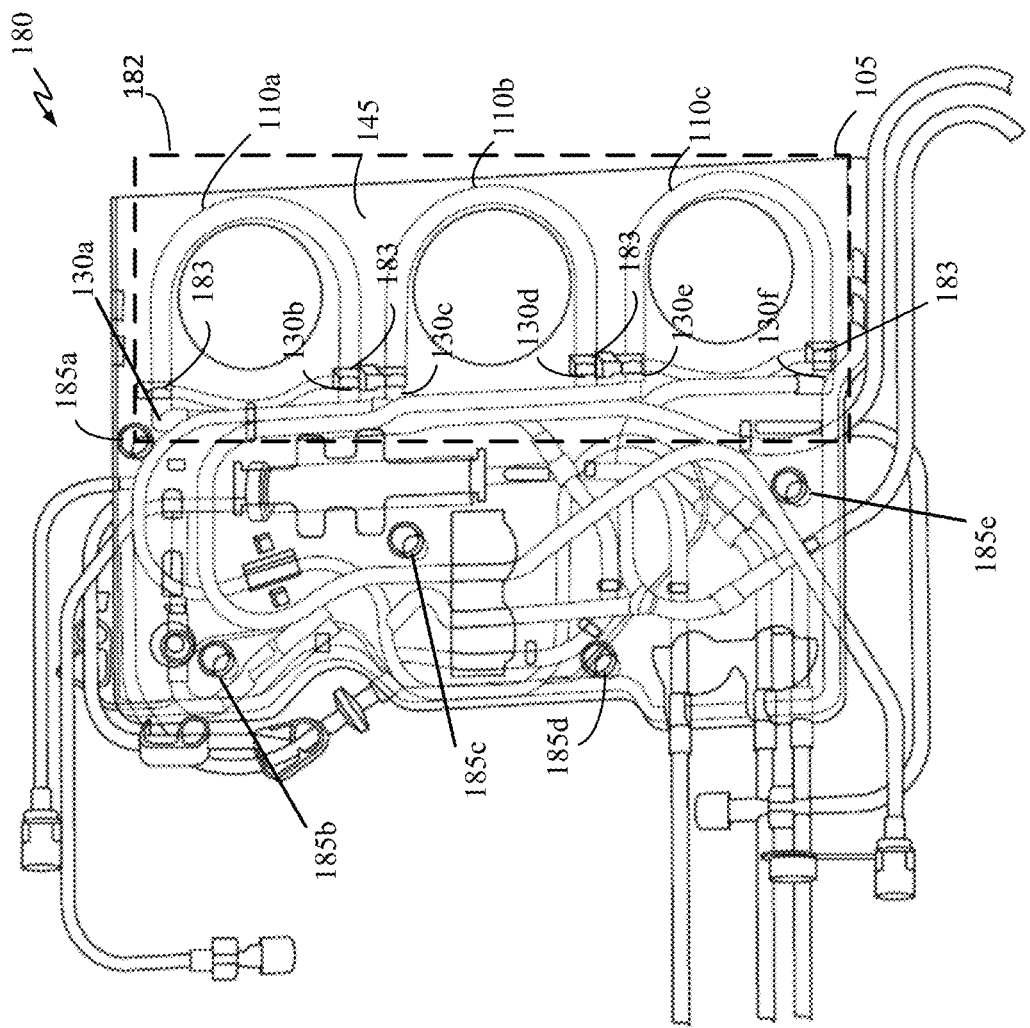
FIG. 1E is a side view of a disposable cartridge in accordance with some embodiments of the present disclosure.

FIG. 1E illustrates a cartridge 180 in accordance with some embodiments of the present disclosure. Cartridge 180 can be a disposable cartridge. In some embodiments, tubing lines 110*a*, 110*b*, 110*c* of cartridge 180 can be coupled to couplings 130*a* through 130*f* (130*a-f*), which are no longer mounted on a moveable tubing-support structure similar to structure 125 of FIG. 1A. In this embodiment, section 182 (e.g., pump track section) of the entire tube structure is able to move about a plane that is parallel to main surface 145. This is due to the flexible nature of section 182 of the tube structure. Additionally, in section 182, no portion of the tube structure is directly affixed to housing 105. This enables section 182 to have inherent flexibility that allows it to move and flex as it is being installed and engaged with a pump track cassette (e.g., assembly 200 of FIG. 2A).

In some embodiments, cartridge 180 includes a plurality of alignment-engagement openings (e.g., alignment features) 185*a* through 185*e* (185*a-e*). Each of the alignment openings (e.g., holes, slots) 185*a* -*e* is configured to receive a pull-pin (not shown) that is designed to be inserted beyond the plane of main surface 145 to pull housing 105 into the body of the dialysis machine. In this way, cartridge 180 can be securely affixed to the dialysis machine. Although five specific alignment openings 185*a* -*e* are shown, cartridge 180 can have any number of alignment openings (e.g., 2, 3).

In some embodiments, housing 105 can include a plurality of support structures 183 disposed in section 182. Each support structure 183 can be made to loosely or securely hold a tubing line. In some embodiments, support structure 183 is made to loosely hold the tubing line such that during the installation of cartridge 100, tubing lines 110*a*, 110*b*, and 110*c* can be wiggled into place if there is any misalignment. Cartridge 180 can also include one or more features of cartridge 100 as described with respect to FIGS. 1A and 1B.

Pump Track Assembly

Figure 2A:
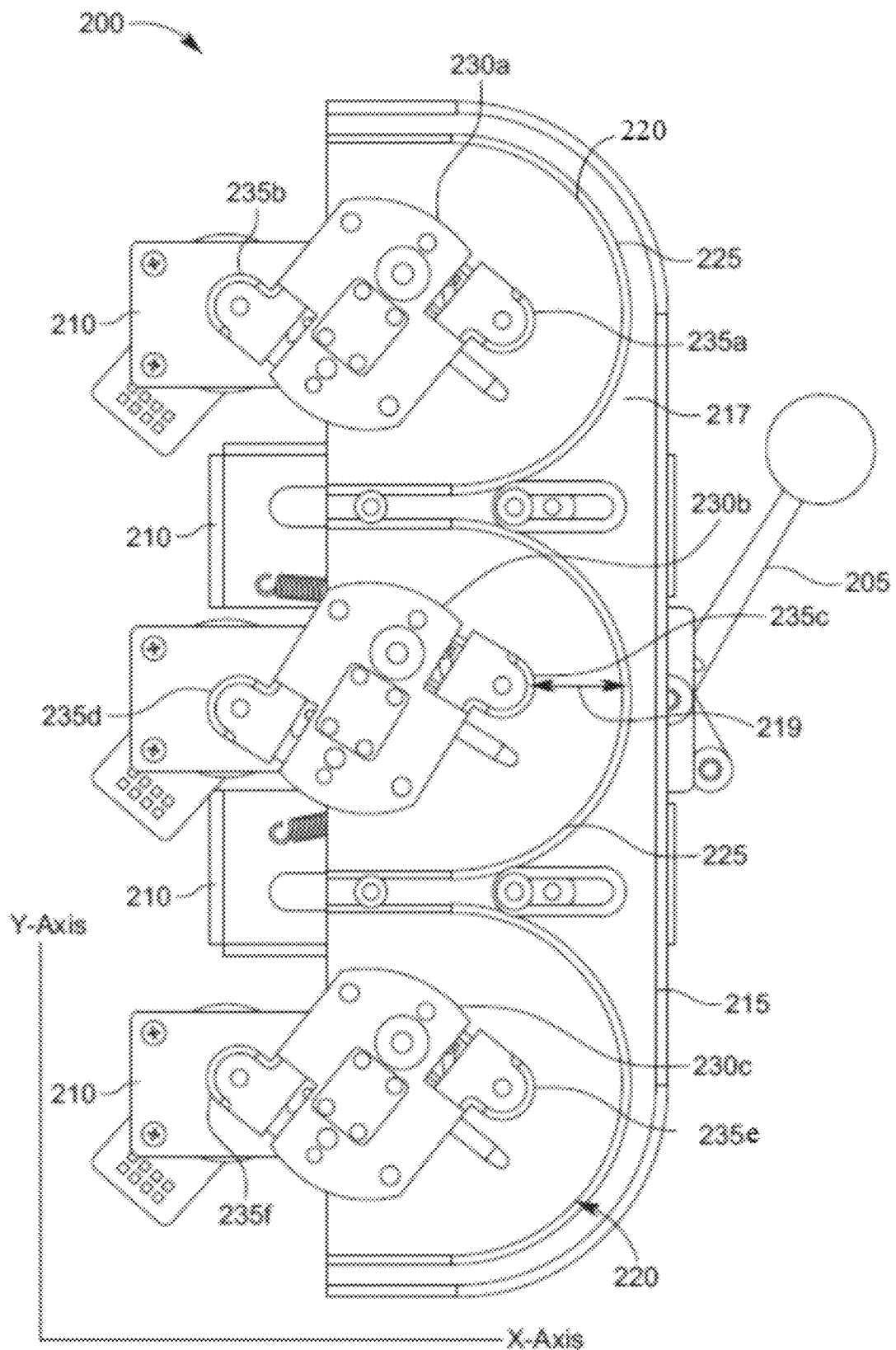
FIGS. 2A and 2B are side views of a pump track structure in accordance with some embodiments of the present disclosure.
Figure 2B:
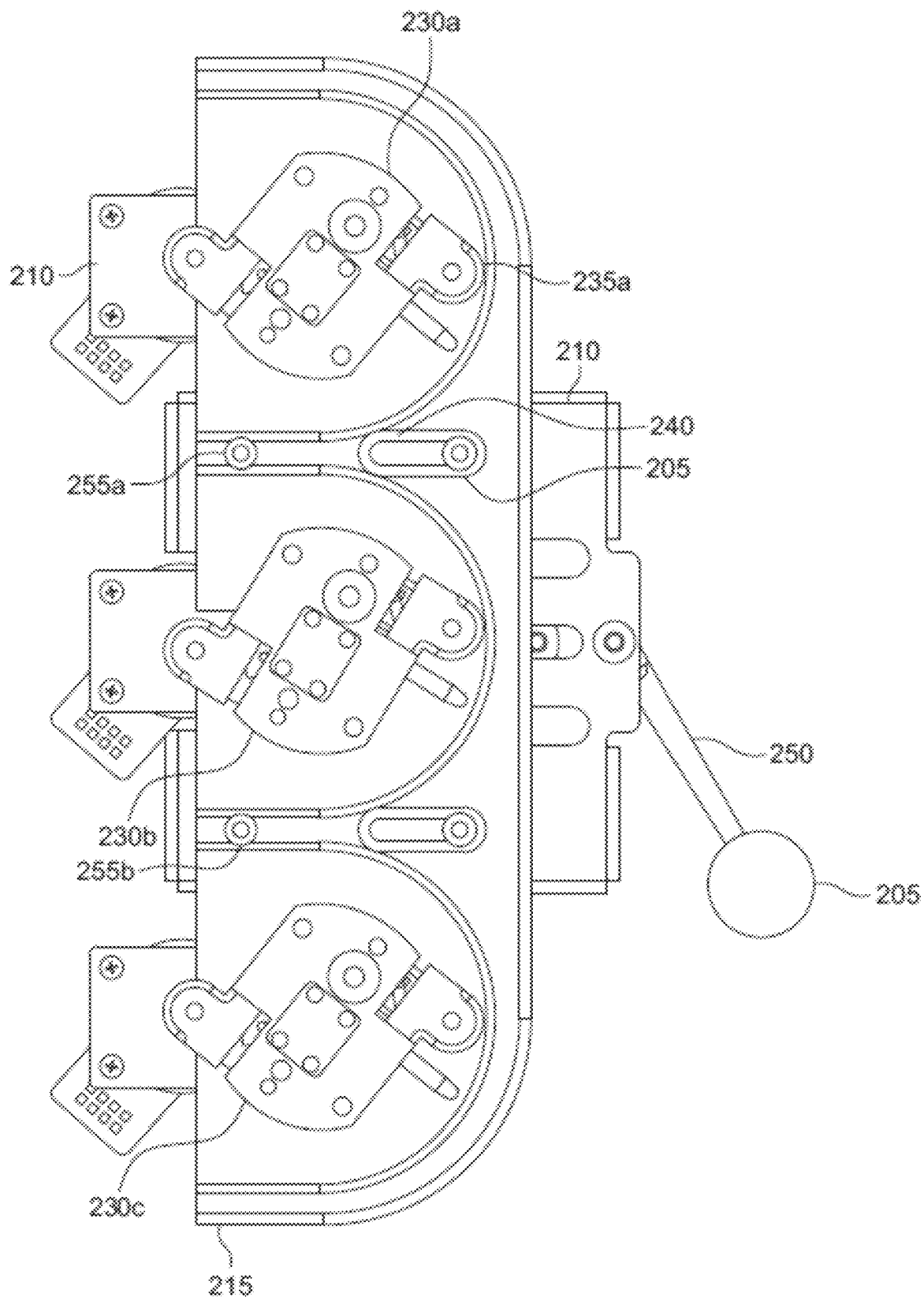

FIGS. 2A and 2B are side views of a pump track assembly 200 located on the reusable dialysis machine in accordance with some embodiments of the present disclosure. FIG. 2A illustrates pump track assembly 200 with lever 205 in the disengaged (up) position. Pump track assembly 200 can include a frame 210, a cassette 215, and a lever 205. Frame 210 can be fixedly secured to the frame of the dialysis machine such that frame 210 remains stationary during the actuation of pump track assembly 200. Frame 210 can include one or more rotary actuators (e.g., motors), which are located behind cassette 215. In some embodiments, frame 210 can have three rotary actuators. Each rotary actuator can be securely attached to frame 210.

Cassette 215 can be coupled to frame 210 via a linkage assembly (not shown), which will be discussed in further detail below. The linkage assembly enables cassette 215 to be translatable in one direction with respect to frame 210. The translation of cassette 215 can be actuated by lever 205, which is coupled to the linkage assembly. Cassette 215 can have one or more track structures 220. Each track structure 220 includes a recessed track 225, rotor 230, and at least two rollers 235. In some embodiments, cassette 215 has three track structures, each configured to receive a corresponding tubing line of disposable cartridge 100. Recessed track 225 can have a shape that corresponds to the shape of the predetermined pathway of the tubing line (e.g., tubing line 110) of disposable cartridge 100. For example, since tubing line 110a of disposable cartridge 100 has a U-shape pathway, then recessed track 225 can also have the same U-shape track. Recessed track 225 is recessed below a surface 217 of cassette 215. The depth of the recess can be at least the thickness of tubing line 110a. In this way the tubing line can be seated neatly within the recessed track.

As previously mentioned, FIG. 2A shows cassette 215 in an open position for the installation of disposable cartridge 100 and its tubing lines. Once disposable cartridge 100 is installed, tubing lines 110 will be located inside of recessed track 225. Since each of the tubing lines 110 can also move along the x-axis (because of the floating tubing-support structure), tubing line 110 can be easily guided into recessed track 225 between space 219. The combination of the floating tubing lines 110 and the translatable cassette 215 makes the installation disposable cartridge 100 much easier. This design also enables disposable cartridge 100 to be installed with only one hand since tubing 110 has some play and in addition to the wide space 219 being available when cassette 215 is in the disengaged position (lever 205 being in the up position as shown).

Each of rotors 230a-c includes at least two rollers. For example, rotor 230a includes rollers 235a and 235b. Rollers 235a and 235b can be positioned on the opposite side of rotor 230. Each of the rotor 230 can be coupled to a shaft (not shown), which can be coupled to a rotary actuator (not shown) via one or more gears. In some embodiments, rotor 230 can also be directly coupled to the shaft of rotary actuator (not shown).

FIG. 2B illustrates pump track assembly 200 in a close position with lever 205 in an engaged (down) position. When lever 205 is down, the linkages assembly (not shown) is actuated such that cassette 215 is translated toward rotor 230 and roller 235 while frame 210 remains stationary. Rotor 230 includes a central shaft (not shown) in the center of rotor 230. When cassette 215 is in the close position (as shown), the center of rotor 230 corresponds to the center of recessed track 225. In this way, when rotor 230 is rotating, the roller 235 that is closes to the curved portion of recessed track is at a constant distance away from the curved portion. This enables roller 235 to pinch (e.g., compress) tubing line (not shown) and stop the flow of fluid at the pinched location while pushing the fluid forward when rotor 230 rotates and roller 235 runs along the curved portion ## of recessed track 225. Rollers 235 are positioned on rotor 230 such that at least one roller 235 is impinging upon tubing line 110 to stop the flow of fluid.

Cassette 215 can include a slot 240 which is configured to receive a pin 245 that is fixedly secured to frame 210. Slot 240 enables cassette 215 to translate back and forth along the axial length of slot 240. When lever 205 is actuated to the lock (bottom, as shown in FIG. 2A) position from the open (up) position, cassette 215 is moved to the close position by one of the linkages (not shown) on the opposite side (hidden from view) of cassette 215. As shown, lever 205 can have a relatively long handle 250 to provide a mechanical advantage for the user. This allows the user to easily operate the lever.

Cassette 215 can be slidably mounted to frame 210 at locations 255a and 255b. At each location 255a or 255b, cassette is fixedly mounted to a linkage assembly (not shown) with a nut or bolt. However, at the same time, the nut/bolt is slidably coupled to a slot (not shown) on frame 210 (see FIG. 3A). This allows cassette 215 to be translatable with respect to frame 210.

FIGS. 3A, 3C, 3E, and 3F are perspective views of the backside of pump assembly 200 at various actuating positions in accordance with some embodiments of the present disclosure.

Figure 3A:
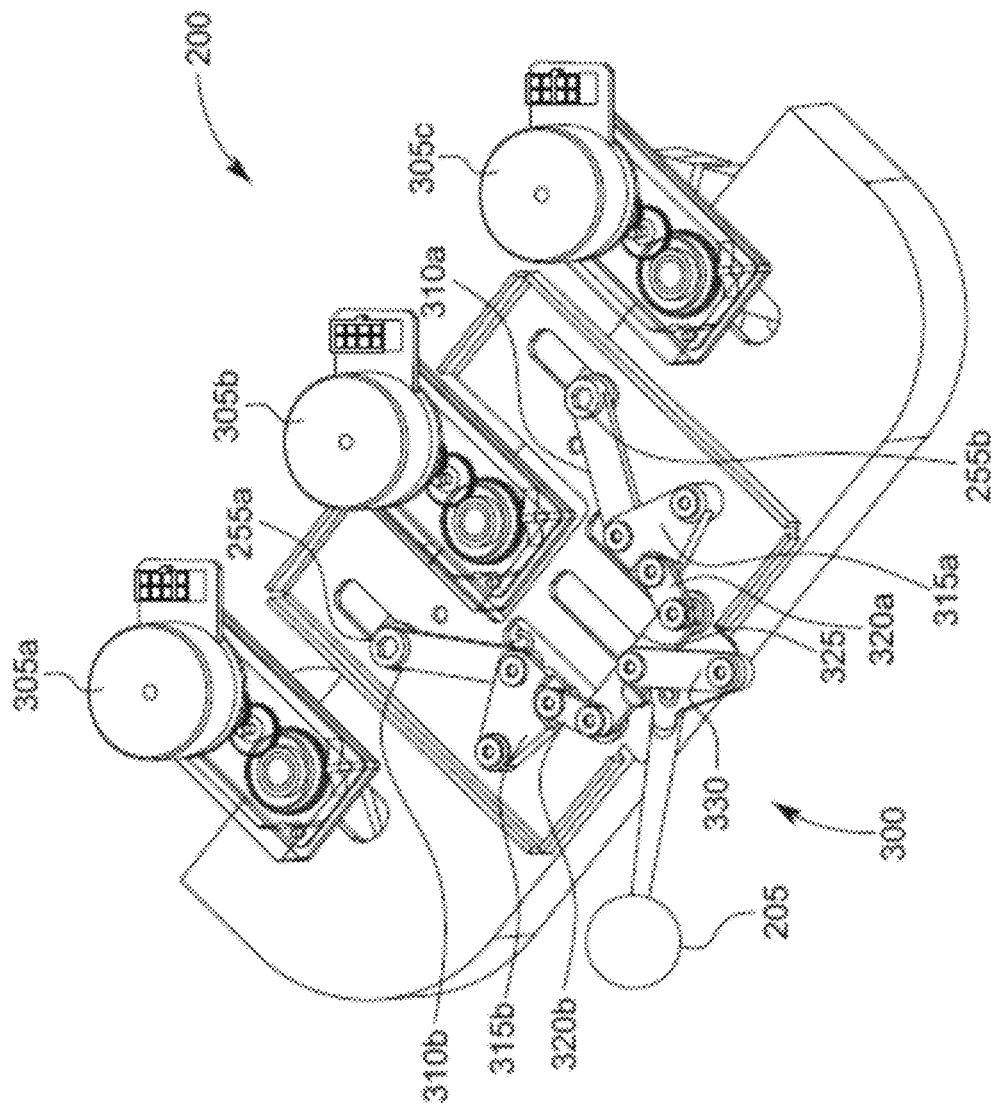
FIGS. 3A, 3B, 3C, 3D, 3E, 3F, and 3G are perspective front and back views of the pump track structure of FIG. 2A in accordance with some embodiments of the present disclosure.

FIG. 3A illustrates cassette 215 in an open position. FIG. 3C illustrates cassette 215 in a semi-close position with level being actuated half-way. FIG. 3E illustrates cassette 215 being in a fully close position but not locked. FIG. 3F illustrates cassette 215 being in a fully close and locked position with certain linkages elements lined up thereby making it harder for the linkage assembly to disengage accidentally. Additionally, linkage assembly 300 are designed such that when lever 205 is in the down position (toward the ground) the linkage assembly is locked. This eliminates the chances of an accidental disengagement of the linkage assembly (rollers 235 would disengage) as gravity would not contribute to the disengagement but rather would help keep lever 205 in the down position and thereby keeping linkage assembly and cassette 215 in a locked position.

Figure 3B:
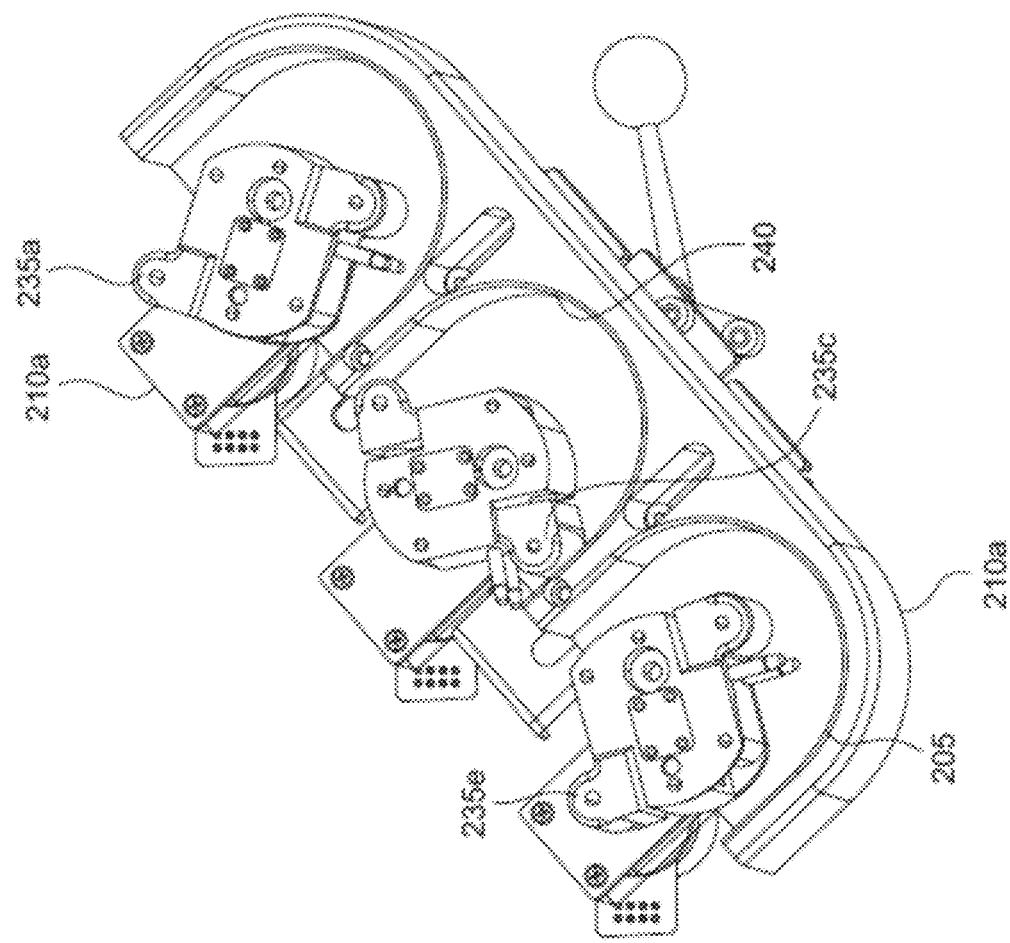
Figure 3C:
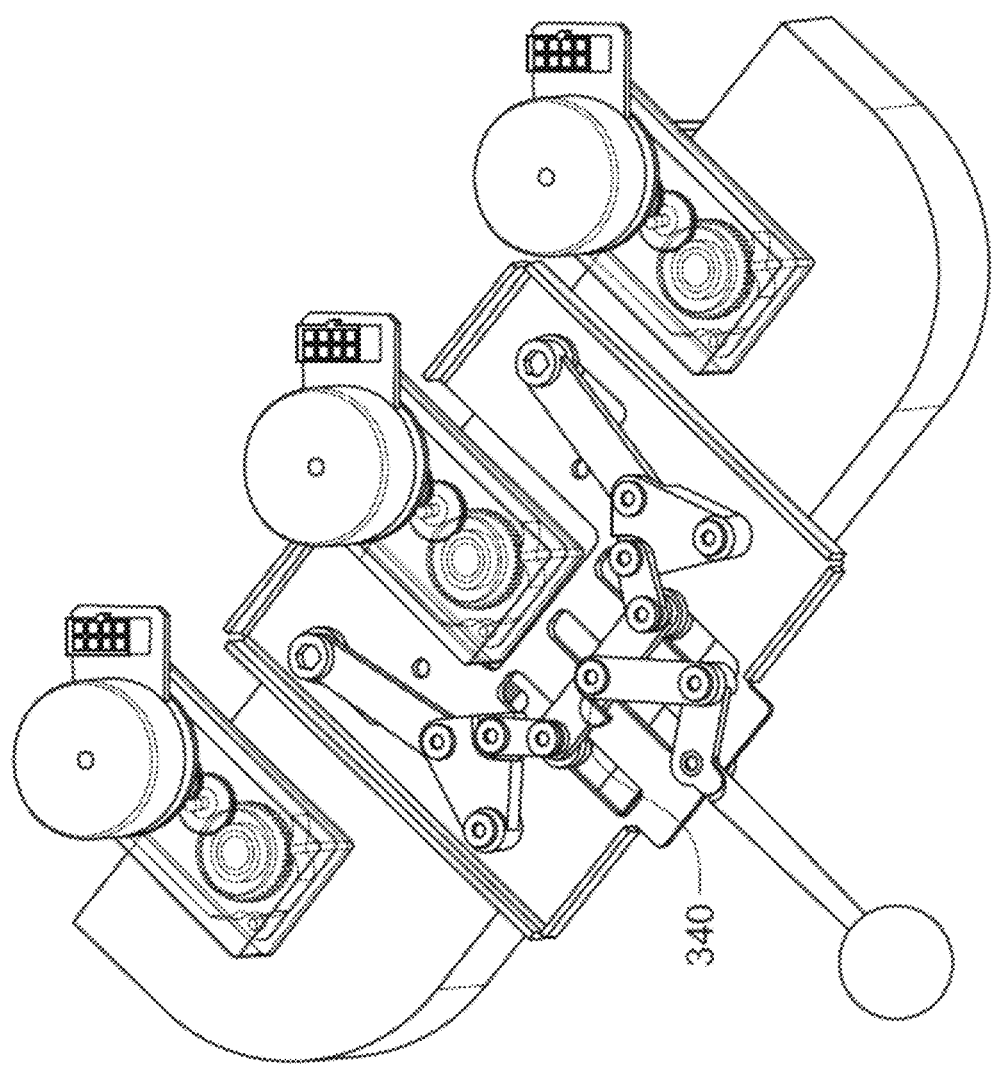
Figure 3D:
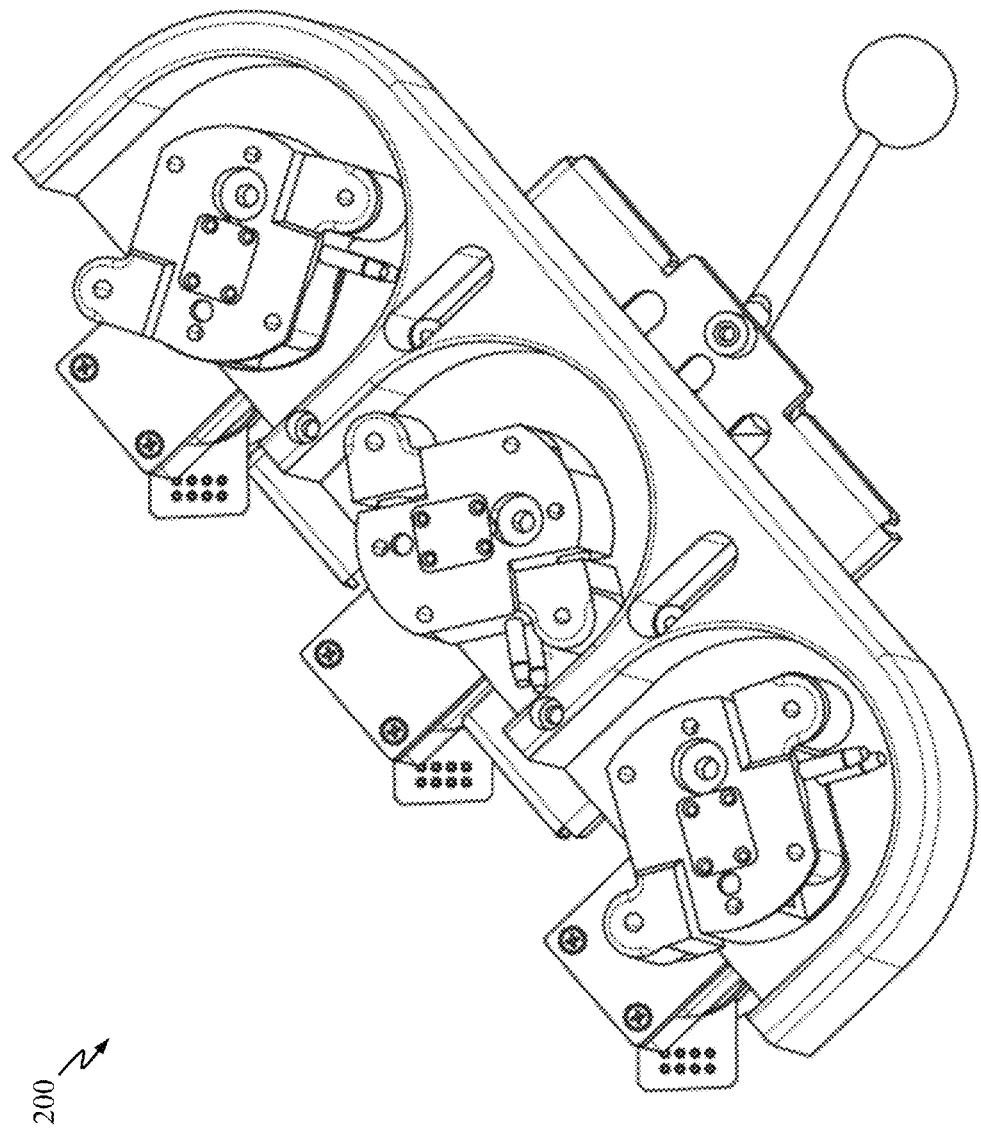
Figure 3E:
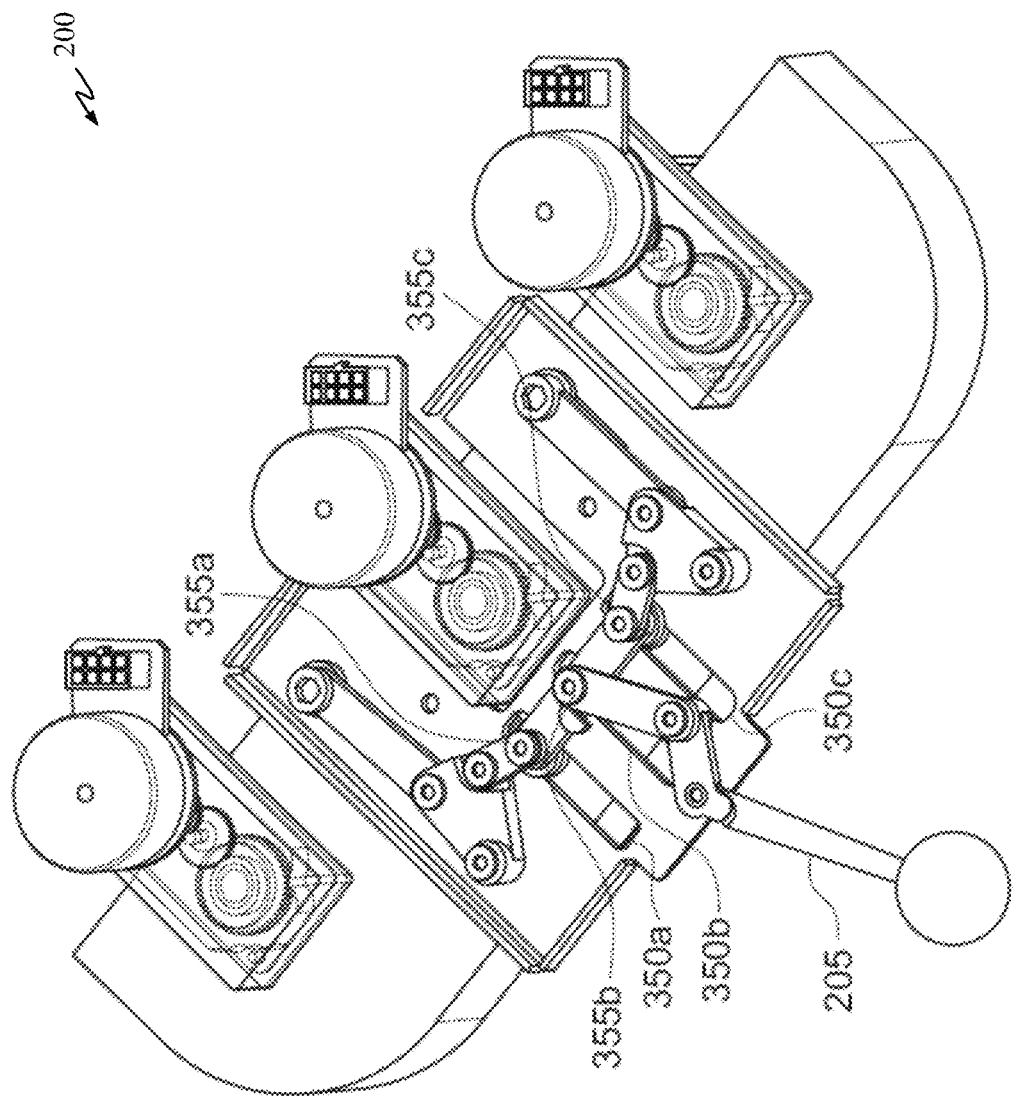
Figure 3F:
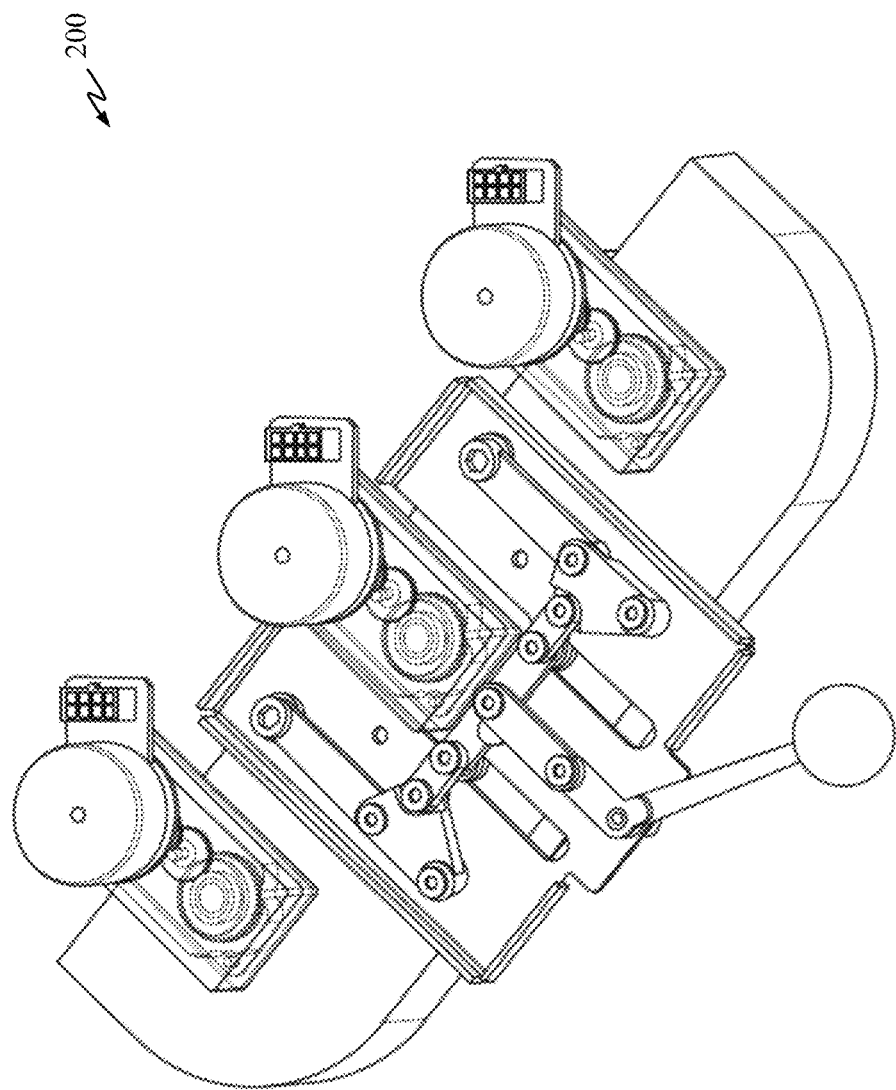
Figure 3G:
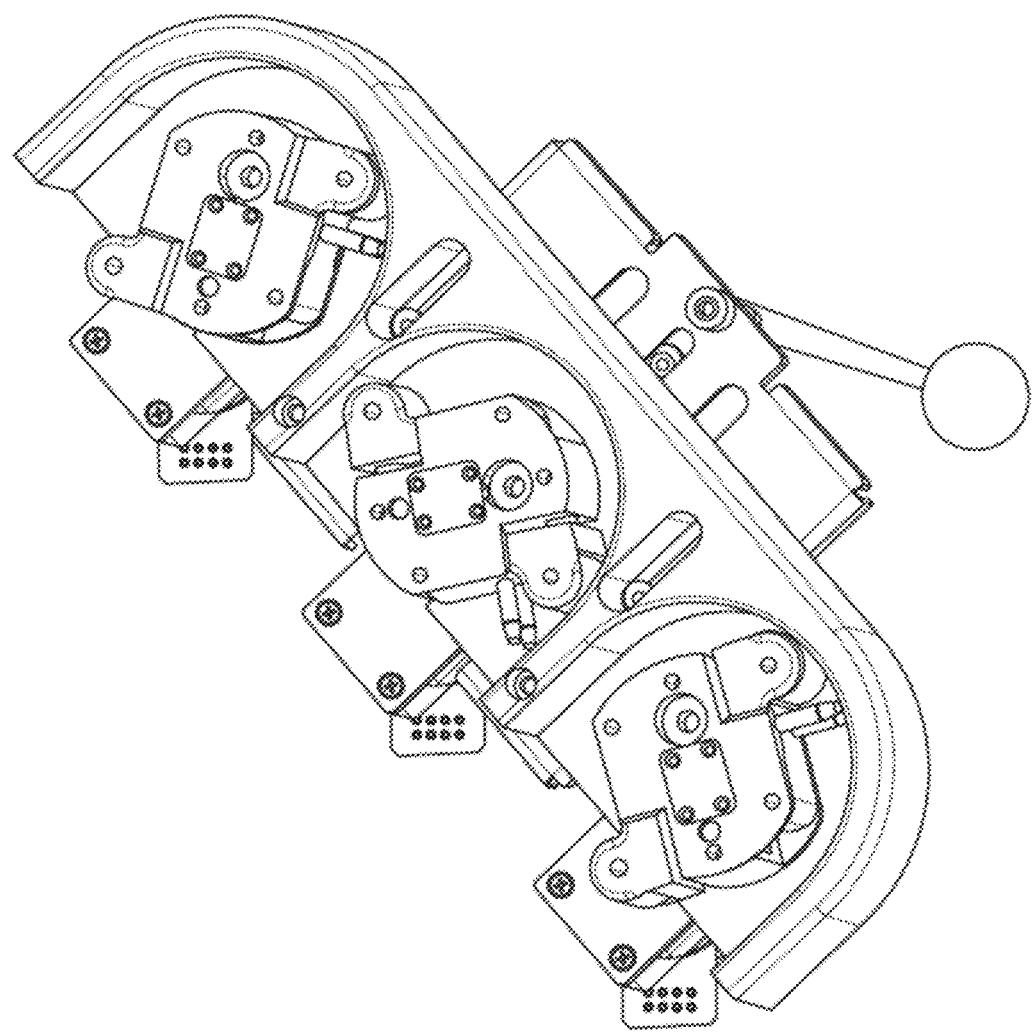

FIGS. 3B, 3D, and 3G are perspective views of the frontside of pump assembly 200 at various actuating positions in accordance with some embodiments of the present disclosure. FIG. 3B illustrates cassette 215 in an open position. See also FIG. 3A, which is also in the same position but with the backside being shown. FIG. 3D illustrates cassette 215 in a semi-close position with level being actuated half-way. FIG. 3C shows the same position but from the front side. FIG. 3G illustrates cassette 215 being in a fully close position and locked. FIG. 3F shows the exact same position but from the front side.

Referring to FIGS. 3A and 3B, pump assembly 200 includes frame 210 and rotary actuators 305a, 305b, and 305c. Each rotary actuator can be actuated at a different time and/or rotational rate such that the positions of the rollers on each rotor can be different (see FIG. 3B). For example, roller 235a, roller 235c, and roller 235e are all in different positions with respect to cassette 215 or its respective recessed track.

As previously mentioned, linkage assembly 300 that can be actuated with lever 205. Linkage assembly 300 includes arms 310a and 310b, pivoting brackets 315a and 315b, minor links 320a and 320b, center link 325, and actuating arm 330, which is coupled to lever 205.

Referring to FIG. 3C, when lever 205 is being pulled down from the up position (FIG. 3A to FIG. 3C), lever 205 pushes the distal end 340 of actuating arm 330 toward the distal direction as shown in FIG. 3C. This action also pushes center link 325 toward the distal direction and causes pivoting bracket 315a and 315b to pivot in the distal direction. At the same time, cassette 215 is being pushed toward the distal direction because cassette 215 is fixedly coupled to arms 310a and 310b at locations 255a and 255b.

As lever 205 is being pulled down further, minor links 320a and 320b begin to align with each other and to center link 325 (see FIG. 3E). FIG. 3F shows minor links 320a and 320b and center link 325 are completely aligned with each other. Once actuating arm 330 is perpendicular to center link 325 the linkage assembly is locked. It can be unlocked; however, the force required to unlock can be a bit more than the force required to move the linkage assembly from the open to the lock position.

Referring to FIG. 3E, linkage assembly 300 can be slidably coupled to frame 210 at locations 355a, 355b, and 355c via slots 350a, 350b, and 350c on frame 210. By coupling a slidable nut assembly at each slot 350a, 350b, and 350c, center link and actuating arm 330 can be slidably attached to frame 210 as shown. In some embodiments, linkage assembly 300 can be actuated using a motor such as a step motor.

Figure 4A:
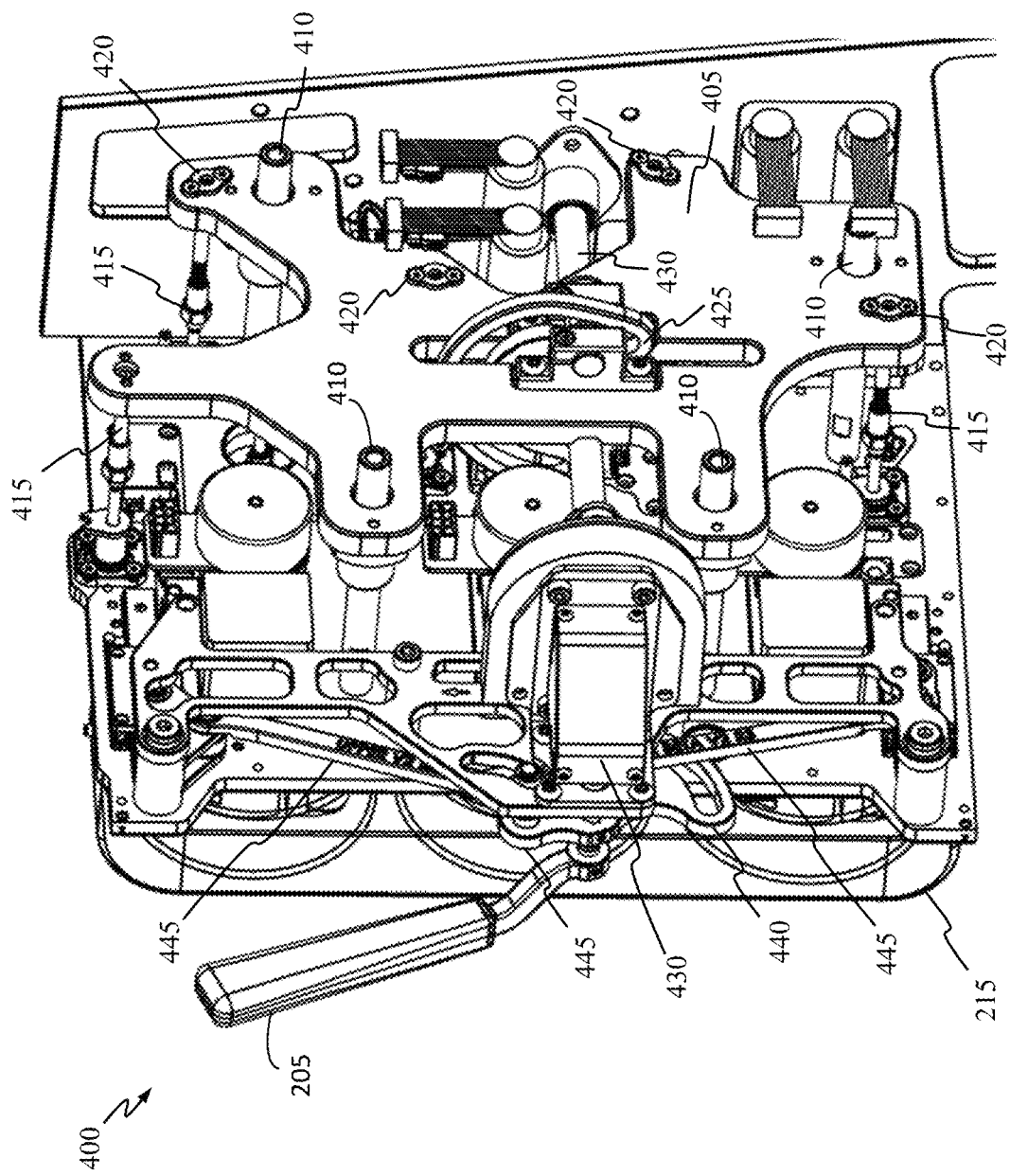
FIG. 4A is a perspective view of a dialysis machine from the back in accordance with some embodiments of the present disclosure.

FIG. 4A is a perspective view of various internal components of a reusable dialysis machine 400 in accordance with some embodiments of the present disclosure. Reusable dialysis machine 400 can incorporate one or more features described above with respect to in FIGS. 1A through 1D, 2A, 2B, and 3A through 3G. In other words, dialysis machine 400 can be configured to use cartridge 100 and/or 180. FIG. 4 shows the internal components of the backside of dialysis machine 400, which includes a pin-pull plate 405, a plurality of guideposts 410, capturing & locking pins 415 (e.g., locking pin), pin-attachment area 420, pull-plate cam 425, cam-shaft 430, gear box 432, lever cam 440, linkage members 445, and chassis 447.

When lever 205 is in the up position as shown in FIG. 4, pin-pull plate 405 is in the forwardmost position. In other words, pin-pull plate 405 is closer to (toward) cassette 215, which is at the front of dialysis machine 400. In the forwardmost position, pin-pull plate 405 pushes pins 415 (e.g., alignment-locking feature) forward to maximally protrude out of the front side of dialysis machine 400. Pins 415 are pushed forward by means of its rear end being attached to pin-attachment area 420, which is affixed to pin-pull plate 405. As pin-pull plate 405 moves forward or backward, pins 415 also move forward and backward due to pins 415 being attached at pin-attachment area 420. During the movement of pin-pull plate 405, it can be guided by one or more guideposts 410, which help pin-pull plate 405 to move in a linear and smooth manner. As will be described further below, pins 415 are designed to grab and pull in cartridge 100 toward the back of dialysis machine 400 (e.g., into cassette 215) as pin-pull plate 405 moves from the forwardmost position to the rearmost position, which is toward the back of dialysis machine 400 (away from cartridge 100).

Lever 205 is used to actuate pin-pull plate 405 from the forwardmost and rearmost positions. When lever 205 is in the up position as shown in FIG. 4, the intermediary linkages assembly (that couples lever 205 to pin-pull plate 405) is configured to move pin-pull plate 405 to the forwardmost position. When lever 205 is in the bottom position (see FIG. 10), the intermediary linkages assembly is configured to move pin-pull plate 405 to the rearmost position (not shown). The intermediary linkages assembly can include pull-plate cam 425, cam-shaft 430, gear box 432, lever cam 440, and linkage members 445 between lever 205 and gear box 432.

Figure 4B:
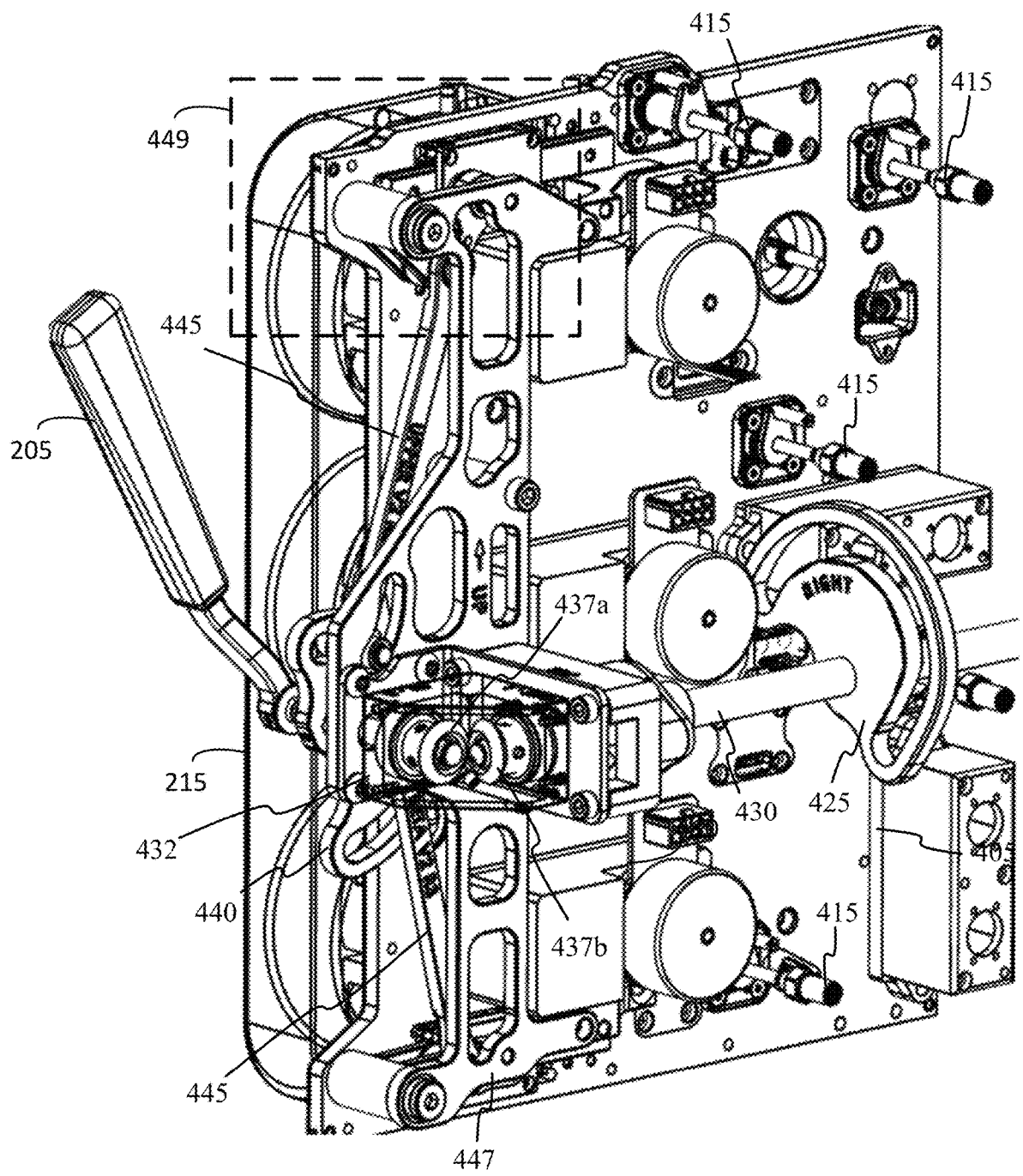
FIG. 4B is a perspective view of the dialysis machine shown in FIG. 4A without the pin-pull plate in accordance with some embodiments of the present disclosure.
Figure 4C:
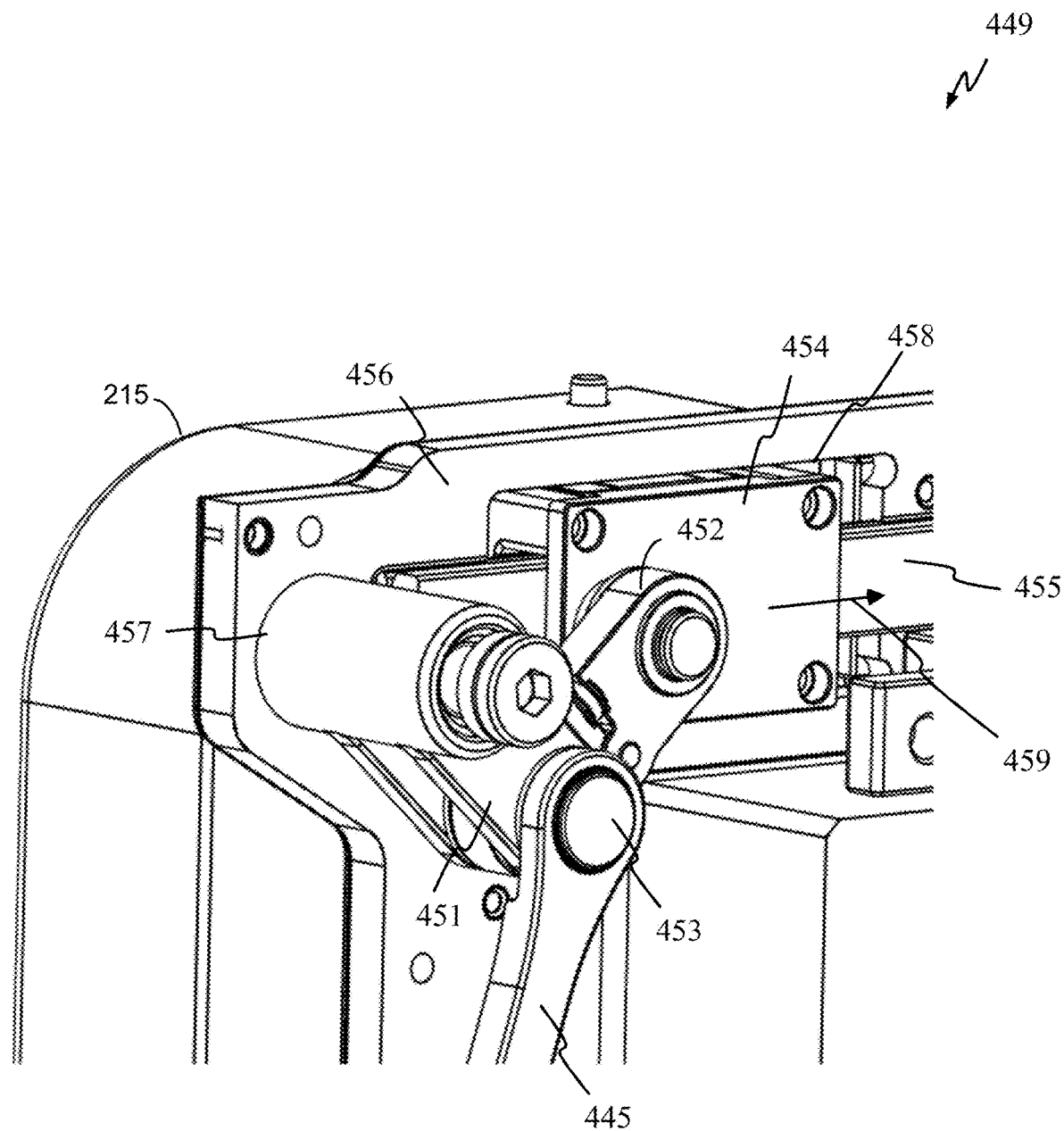
FIG. 4C is a close-up of a section of the dialysis machine shown in FIG. 4B.
Figure 4D:
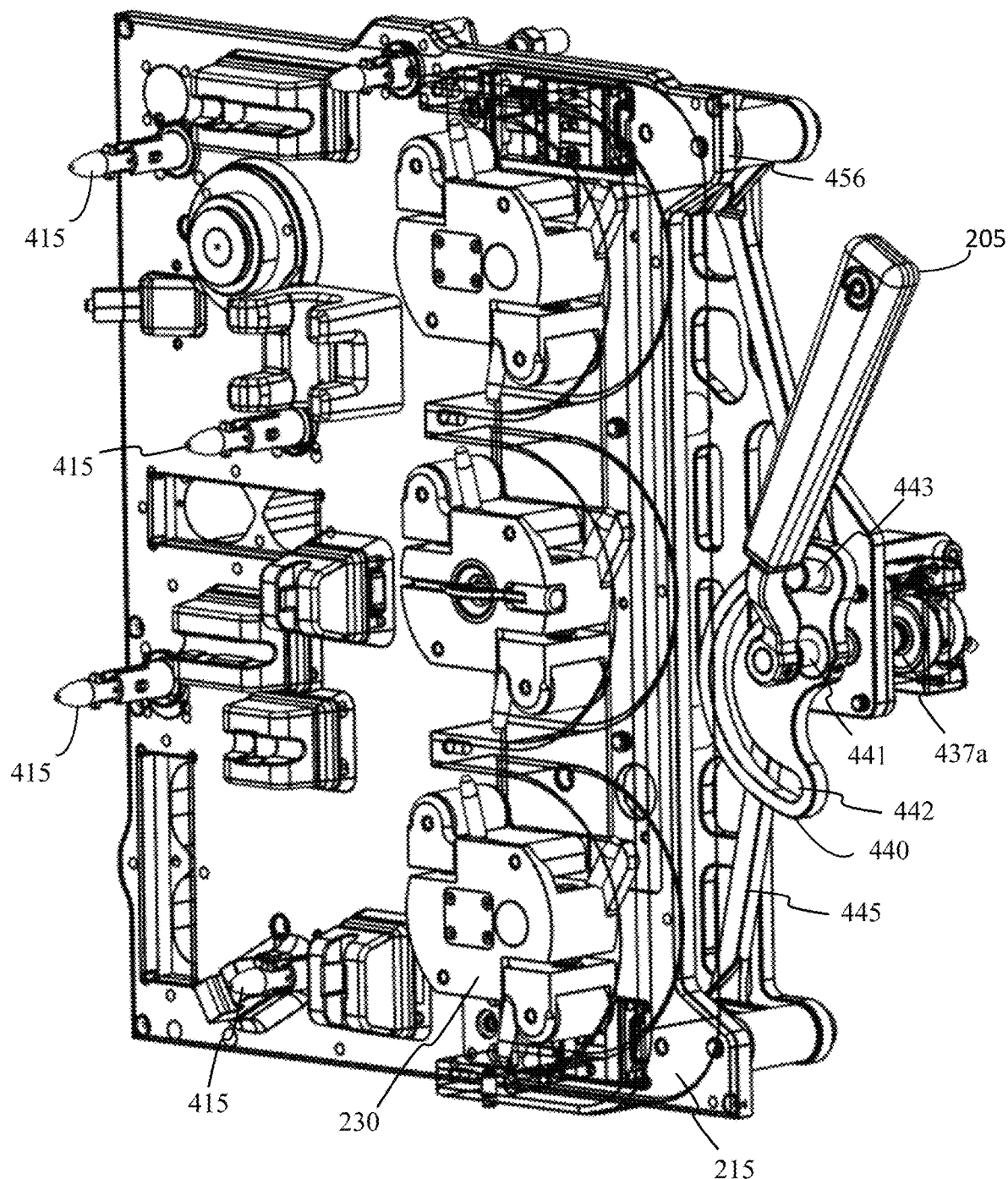
FIGS. 4D and 4E are perspective views of the dialysis machine shown in FIG. 4A from the front in accordance with some embodiments of the present disclosure.

FIG. 4B is a perspective view reusable dialysis machine 400 shown in FIG. 4A with pin-pull plate 405 hidden from view and gearbox 432 internal components being exposed. FIG. 4C is a closeup view of section 449 of FIG. 4B with chassis 447 being hidden from view. FIG. 4D is a perspective view from the front of internal components of dialysis machine 400. These figures will be discussed concurrently.

Lever 205 is coupled to pin-pull plate 405 via lever-cam 440, shaft 441, bevel gears 437a, 437b, cam-shaft 430, and pull-plate cam 425. The motion of lever-cam 440 motion is partially guided by slot 442, which is slidably attached to post 443 of chassis 447. Linkage members 445 are also pivotably coupled to post 443. When lever 205 is actuated, shaft 441 and lever-cam 440 rotate together since shaft 441 is fixedly attached to lever-cam 440.

Referring to FIG. 4C, linkage member 445 is pivotably attached to pivot link 451 and drive link 452 at pivot-pin 453 Drive link 452 is pivotably coupled to slide member 454 (e.g., sliding element) which is slidably mounted on track 455 When lever 205 is actuated, cam-lever 440 would rotate and push linkage member 445 either up or down. As shown, linkage member 445 is in the down position (lever 205 is up). When lever 205 is pulled down, lever-cam 440 would rotate and drive linkage member 445 upward, which pushes pivot link 451 and drive link 452 upward and straighten them out (not shown). This action also causes slide member 454 to slide on track 455 toward the right of FIG. 4C. It should be noted that cassette 200

Track 455 and pivot-post 457 are both directly mounted to front plate 456, which can support a plurality of other structures such as chassis 447. Cassette 215 is slidably attached to front plate 456, such that cassette 215 can translate along track 455. Front plate 456 includes a window 458, which allows cassette 215 to be directly coupled to slide member 454. As lever 205 is actuated, cassette 215 is translated along track 455. When lever 205 is in the up (open) position, cassette 215 is translated toward lever 205. In other words (referring to FIG. 4C), cassette 215 moves toward pivot-post 457 in the opposite direction of arrow 459. When lever 205 is in the down (lock or closed) position, cassette 215 is translated away from pivot-post 457 in the direction of arrow 459. Once cassette 215 is moved to the locking position, which is when slide member 454 is all the way to the right of FIG. 4C in the direction of arrow 459, tubing lines 110a, b, c are pressed against 10the roller (e.g., 235a-f) of each rotor (e.g., 230a, b, c).

Referring to FIG. 4D, lever 205, shaft 441, and bevel gear 437a are coupled to each other. When lever 205 is actuated, shaft 441 and bevel gear 437a would also rotate. This in turn rotate bevel gear 437b (see FIG. 4B), shaft 430, and pull-plate cam 425. Pin-pull plate 405 is coupled to pull-plate cam 425 such that when pull-plate cam 425 rotates, pin-pull plate 405 would move up and down. This in turn pushes pins 415 forward (toward cartridge 100, not shown) or retracts them (away from cartridge 100).

When pin-pull plate 405 is in the forwardmost position, pins 415 are also in their forwardmost position. In this position, the sidearms or side fingers (not shown) of each pin 415 are retracted into the cylindrical body of pin 415. The side fingers are only pushed out of the cylindrical body of pin 415 when pin-pull plate 405 is in the rearmost position. The side fingers are configured to expand outward to capture and pull in cartridge 100 (not shown). More discussion of pin 415 and the side fingers are provided below with respect to FIG. 6.

Figure 4E:
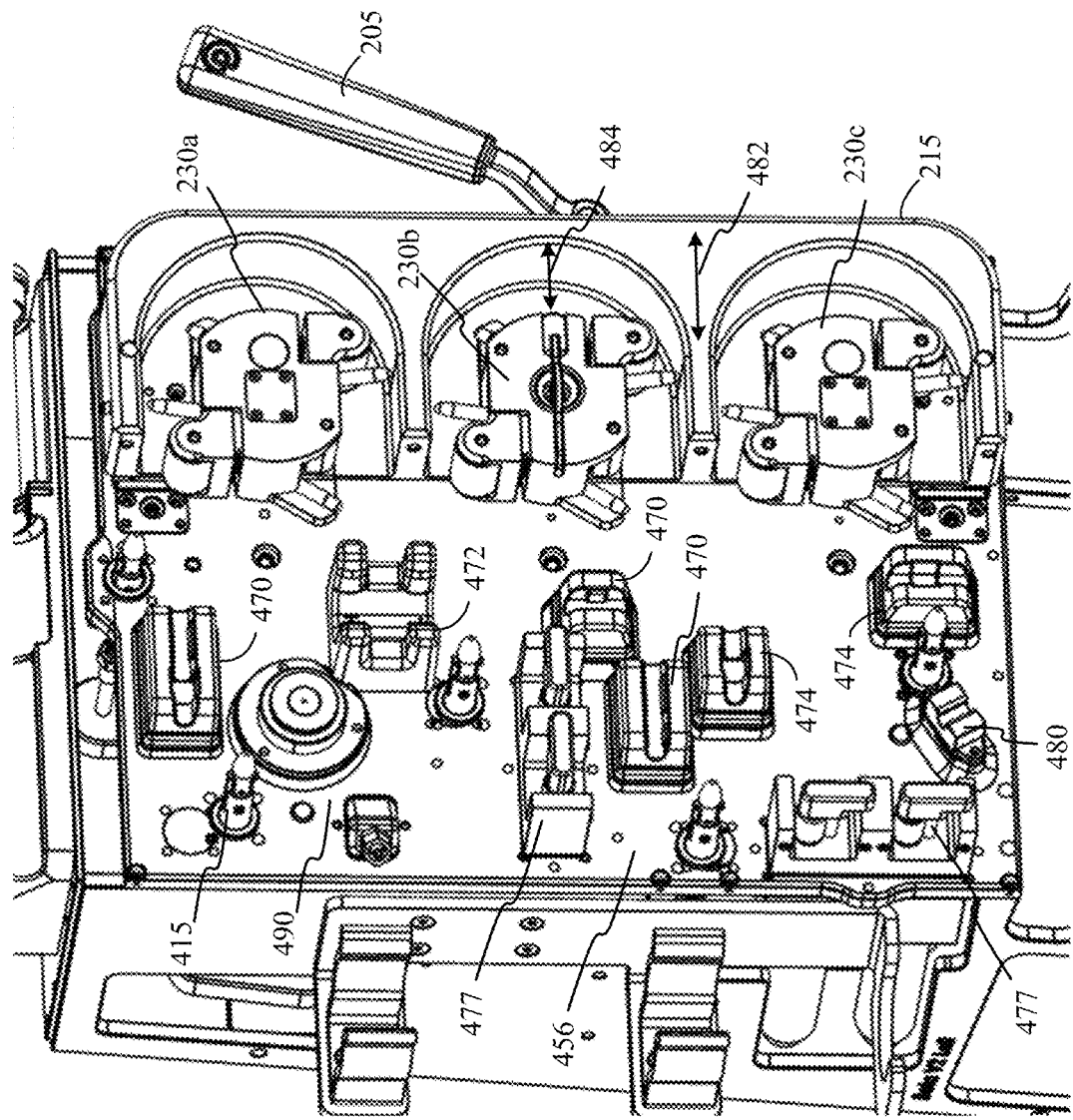

FIG. 4E is a perspective view of dialysis machine 400 that shows various internal components viewed from the front side of the machine. In FIG. 4E, dialysis machine 400 is shown without a cartridge being installed. Dialysis machine 400 can include 3 sets of tubing lines 110a, 110b, and 110c. Each tubing line can have one or more flow and bubble sensors 470, air trap sensor 472, and occlusion (e.g., strain) sensors 474. Dialysis machine 400 can also include one or more pinch valves 477 and a blood leak sensor 480. Once a disposable cartridge (e.g., 100, 800) is installed, the tubing lines of the cartridge will mate with and fall into the slot of each sensor (e.g., 470, 472, 474, 480).

As previously mentioned, cassette 215 is slidably mounted to front plate 456. This enables cassette 215 to move back and forth in the direction of arrows 482. While cassette 215 moves back and forth, rotors 230a, 230b, and 230c are configured to remain stationary with respect front plate 456. To install a disposable cartridge (e.g., cartridge 100, 180), lever 205 is moved to the open position (as shown in FIG. 4E). With lever 205 in this position, cassette 215 is pulled forward toward level 205, which widens gap 484. This allows tubing lines 110a, 110b, 110c to easily fall into gap 484 once the disposable cartridge is dropped into receiving cavity 490 of dialysis machine 400. In other words, the disposable cartridge is dropped onto the surface of front plate 456 until it is stopped by a ledge of pull-in 415 (see item 640 of FIG. 6B).

After the disposable cartridge is dropped into receiving cavity 490 of dialysis machine 400, lever 405 can be closed. This closing motion of lever 205 causes cassette 215 to move toward rotor 230s and narrowing gap 484, which causes one of the rollers of the roller to pinch on the outer surface of one of the tubing lines. At the same time cassette 215 moves toward rotor 230s, pull-pin 415 is retracted and the side fingers (see items 615s of FIG. 6) to expand and grab onto the outer surface of the disposable cartridge. As lever 205 moves into the final locking position (see FIG. 5B), pins 415 fully retract and pull the disposable cartridge inward and securing it with the side fingers. This also causes various tubing lines to fall into the slots of sensors 470, 472, 474, and 480.

Figure 5A:
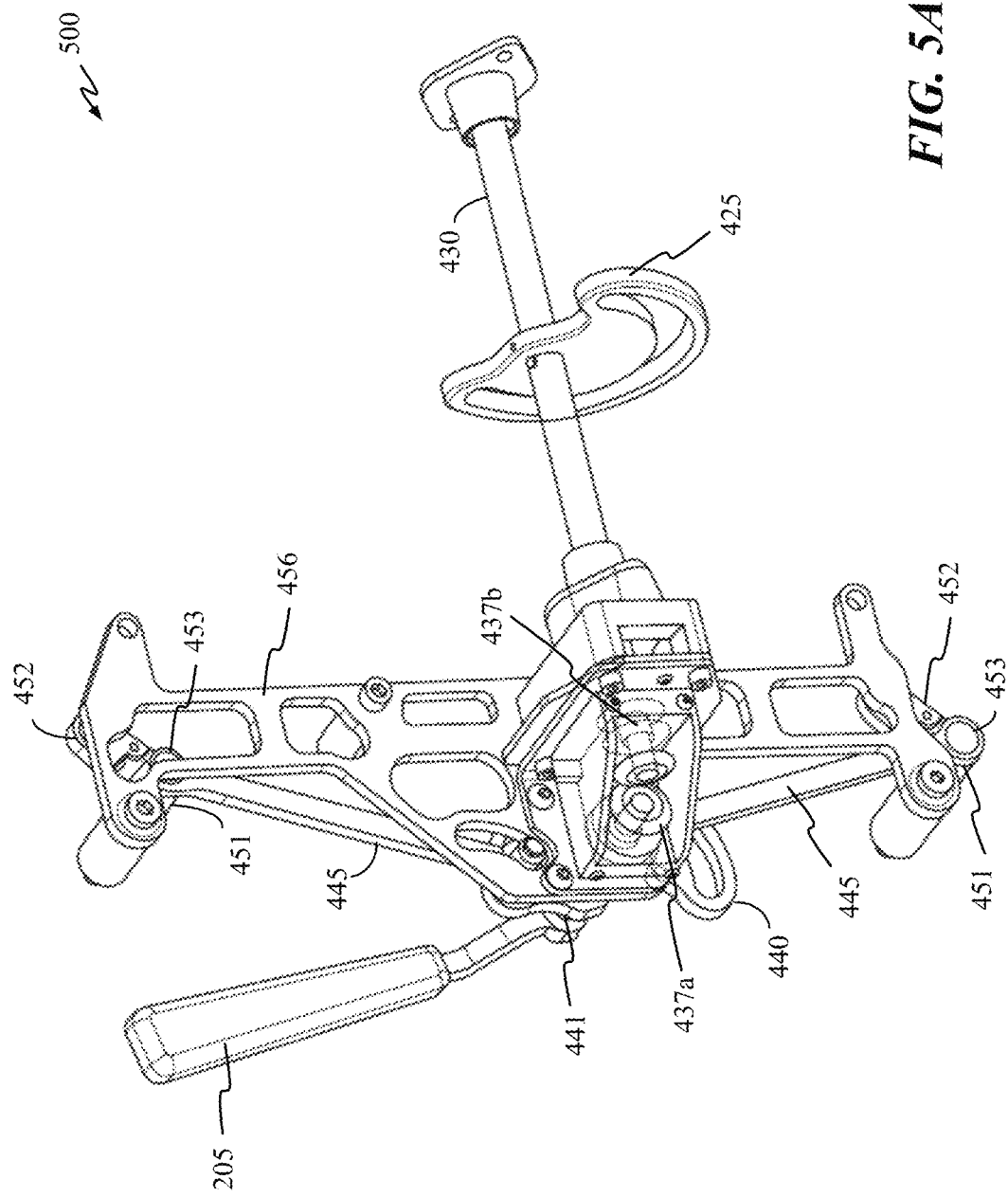

FIG. 5A is a perspective view of linkage assembly (e.g., actuation mechanism) 500 as partially shown and described in FIGS. 4A-D in accordance with some embodiments of the present disclosure. FIG. 5A is an isolated view of linkage assembly 500 with other components hidden from view in order to better exhibit the various components of the assembly. As previously described, assembly 500 includes lever 205, shaft 441, lever-cam 440, bevel gears 437a and 437b, linkage members 445, pivot links 451, drive links 452, front plate 456, shaft 430, and pull-plate cam 425. FIG. 5B is a close-up view of linkage assembly 500 with lever 205 in the down (locked) position. As shown, in the lock position, pivot link 451 and drive link 452 become parallel with each other and the distal end 505 of drive link 452 is at the rightmost position (in the direction of arrow 510). Drive link 452 is directed coupled to slide member 454, which is directly coupled to cassette 215. As drive link 452 moves, slide member 454 and cassette 215 are also moved.

Additionally, when lever 205 is in the locked position, cam 425 is rotated as shown. Cam 425 includes guide-slot 515, which is designed to drive pin-pull plate 405 into the rearmost position. This action also pulls pins 415 rearward and expand out the side fingers of each pin.

In some embodiments, the actuation mechanism can be a collection of motors (e.g., actuators) configured to translate the cassette (e.g., 215) with respect to the frame of the dialysis machine. For example, a linear motor can be provided to replace pivot link 451 and drive link 452. In this example, two linear motors can be provided, one at the top and one at the bottom of the cassette. The linear motor can be controlled by a control system, which can actuate the linear motors on demand.

The actuation mechanism can also include one or more motors to actuate pull-pin 415. For example, each pull-pin 415 can be coupled to a motor (e.g., step or linear motor), which can be coupled to a controller (e.g., control system). The controller can be the same controller that control the motor(s) configured to translate the cassette. In this embodiment, one or more motors coupled to one or more pull-pins can replace pin-pull plate 405. In some embodiments, the controller (on command from the user) can actuate each pull-pin to release or secure the disposable cartridge.

Figure 6A:
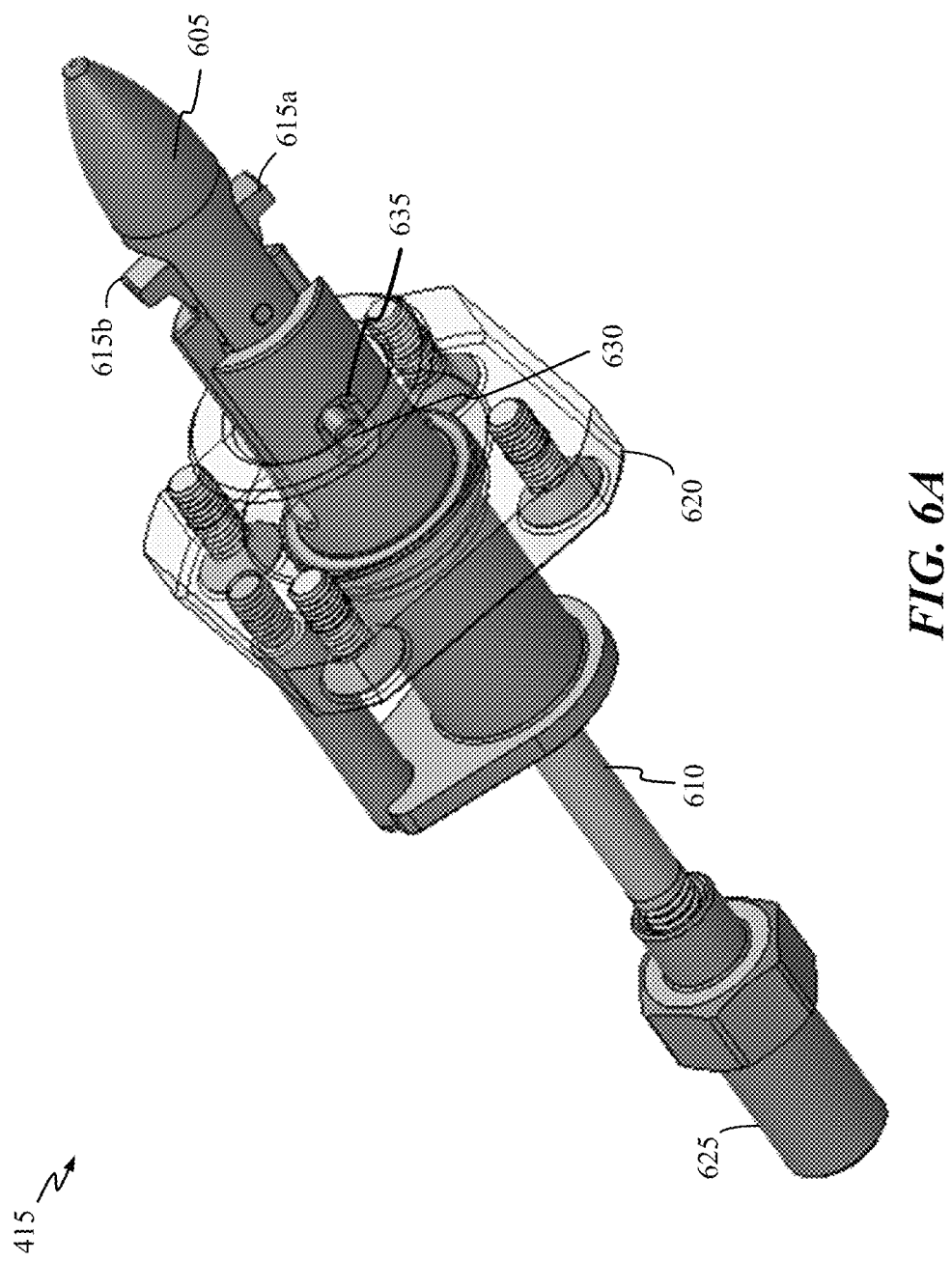
FIG. 6A is a perspective view of an alignment-locking pin in accordance with some embodiments of the present disclosure.
Figure 6B:
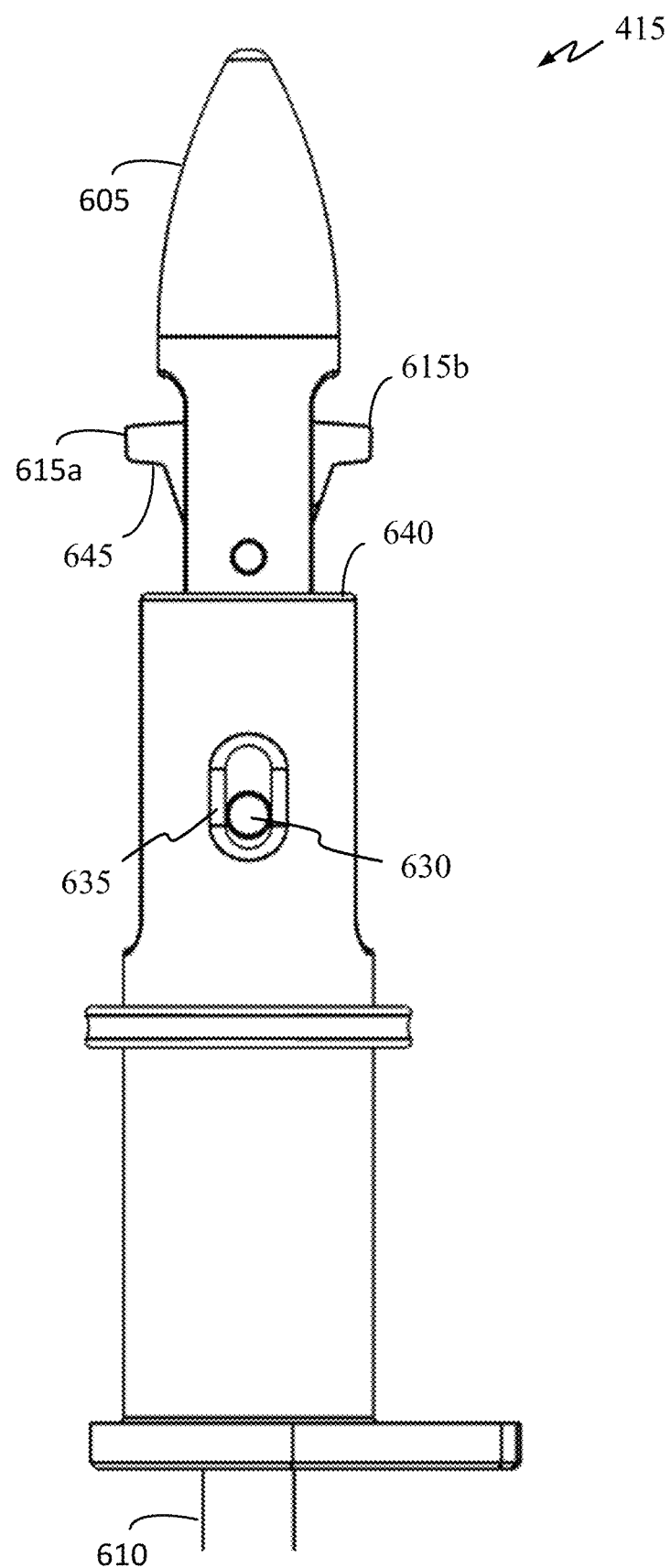
FIG. 6B is a side view of the alignment-locking pin shown in FIG. 6A.

FIG. 6A is a perspective view of pull-pin 415 in accordance with some embodiments of the present disclosure. Pull-pin 415 includes a pin body 605, pull-rod 610, fingers 615a, 615b, front mounting bracket 620, rear mounting bracket 625, stop pin 630, and stop window 635. Pull-pin 415 is mounted to front plate 456 (not shown) by front mounting bracket 620 (which includes a plurality of screws). Pull-pin 415 also includes a pull-rod 610 that is coupled to fingers 615a, 615b via a pin-linkage assembly (not shown) that is located inside of pin body 605. When pull-rod 610 is pulled back by pin-pull plate 405, the pin-linkage assembly causes fingers 615a, 615b to protrude out of pin body 605. This enables pull-415 to pull in and secure a disposable cartridge (e.g., cartridge 100, 180) as it is inserted into dialysis machine 400. When pull-rod 610 is pushed upward (toward the tip of pin body 605), the pin-linkage assembly causes fingers 615a, 615b to fold inward such that it does not cause any interference with the body of cartridge 100. This enables the disposable cartridge to be removed from dialysis machine 400.

When the disposable cartridge is installed, it sits on ledge 640 and is secured by the bottom ledge 645 of each finger (615a, 615b). In this way, the disposable cartridge is secured in place until fingers 615a, 615b are retracted when pin-pull plate 405 is retracted.

Figure 6C:
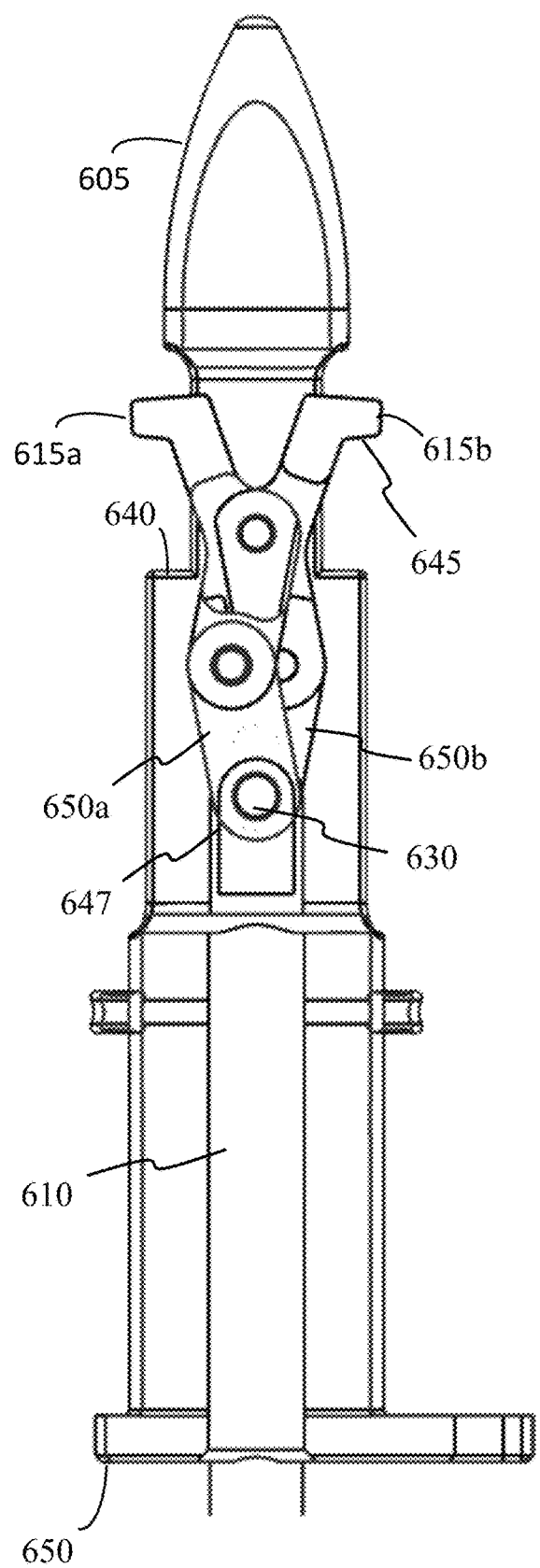
FIG. 6C is a side cut-out view of the alignment-locking pin shown in FIG. 6A in accordance with some embodiments of the present disclosure.

FIG. 6C is a cut-out view of pin 415 to show the pin-linkage assembly interaction with fingers 615a, 615b. As shown, pull-rod 610 is coupled to links 650a, 650b at distal end 647 of pull-rod 610 by stop pin 630. Pull-rod 610 is slidable within the lumen of pin body 605. The second (proximal) end (not shown) of pull-rod 610 is attached to pin-pull plate 405. Thus, when plate 405 is retracted (lever 205 moved to the locking position), pull-rod 610 is pulled downward toward the base 650 of pin 415. This motion, in turn, also pull down links 650a and 650b and straighten it out (causing them to be parallel to each other). At the same time, finger elements 615a, 615b are pushed outward causing them to grab onto an outer surface of a disposable cartridge and secure it. When plate 405 is advanced toward the disposable cartridge (lever 205 moved to the open position), pull-rod 610 is pushed upward toward the tip of pin 415. As pull-rod 610 is pushed upward, links 650a and 650b flare out away from each other at the non-pivoting end. This causes the tip of fingers 615a, 615b to retract inward. In some embodiments, fingers 615a, 615b completely retract within the interior body of pin 415. In this way, fingers 615a, 615b do not interfere with the removal of the disposable cartridge.

Referring concurrently to FIGS. 1D and 6C, the length of pin 415 is selected such that the tip of pin 415 would extend through and beyond an alignment opening (e.g., 185a, 185b) of disposable cartridge 180. Additionally, when lever 205 is in the open position, the tip of the side fingers (e.g., 615a, 615b) of pin 415 would also clear the alignment opening. In this way, when lever 205 is moved to a closed position, side fingers 615a, 615b would have sufficient clearance above the outermost surface of cartridge 180 to grab hold of the disposable cartridge and pull it back.

Additional Embodiments

In some embodiments, a disposable cartridge for a dialysis machine is disclosed. The disposable cartridge includes: a housing; and a tubing-support structure having one or more tubing lines, wherein the tubing-support structure is coupled to the housing such that it can only move along a single axis parallel to a main surface of the housing, wherein the one or more tubing lines are parallel to the main surface of the housing. The tubing-support structure can include one or more spring members coupled to the housing. The one or more spring members enable the tubing-support structure to move along a single axis.

In some embodiments, the one or more spring members is constructed such that movement of the tubing-support structure is restricted on at least 1 axis. The one or more spring members can be a plastic element having a flat geometry. The disposable cartridge can also include a heating bag having an inlet configured to receive fluid from one of the one or more tubing lines. The heating bag includes one or more channels that runs in and out of the heating bag, which can be perpendicularly attached to the main surface of the housing.

The housing can include a plurality of alignment structures for supporting and aligning the tubing-supporting structure and the one or more tubing lines.

In some embodiments, a pump track structure of a dialysis machine is also disclosed. The pump track structure can include a frame fixedly coupled to the dialysis machine; a cassette having one or more track structures; a linkage assembly configured to translate the cassette while the frame remains stationary. Each of the one or more track structures can include a rotor and one or more rollers. The linkage assembly can be slidably coupled to the cassette at one or more points and pivotably coupled to the frame at one or more points.

The linkage assembly can include a first arm slidably coupled to the frame and fixedly coupled to the cassette; a first pivotable bracket pivotably coupled to the frame and pivotably coupled to the first arm; a first minor arm pivotably coupled to the first pivotable bracket; and a center link pivotably coupled to the first minor arm and a second minor arm. The second minor arm is pivotably coupled to a second pivotable bracket, and the second pivotable bracket is pivotably coupled to the frame. The second arm is slidably coupled to the frame and fixedly coupled to the cassette. The center link is slidably attached to the frame and to an actuating link, wherein the actuating link is coupled to a lever.

A controller can be a combination of hardware (e.g., processor, memory) and software components having instructions and logic to control the various components of the dialysis system as described above. For example, the controller can have instructions and logic to control the operation of actuation mechanism to actuate the cassette (e.g., 215) and pin (e.g., 415) as described above.

In closing, regarding the exemplary embodiments of the present invention as shown and described herein, it will be appreciated that a hemodialysis system is disclosed. The principles of the invention may be practiced in a number of configurations beyond those shown and described, so it is to be understood that the invention is not in any way limited by the exemplary embodiments, but is generally directed to a hemodialysis system and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention. Furthermore, the various features of each of the above-described embodiments may be combined in any logical manner and are intended to be included within the scope of the present invention.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the Specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present Specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

While several particular forms of the invention have been illustrated and described, it will be apparent that various modifications can be made without departing from the spirit and scope of the invention. Therefore, it is not intended that the invention be limited except by the following claims.

The invention claimed is:

1. A dialysis system comprising:
a dialysis machine and a disposable cartridge;
said dialysis machine including,
a frame fixedly coupled to the dialysis machine;
a cassette slidably coupled to the frame, the cassette comprises three track structures, wherein each of the three track structures comprises a rotor and one or more rollers;
one or more alignment-locking features extending from the frame, the one or more alignment-locking features configured to be inserted into one or more alignment features of a disposable cartridge and secure or release the disposable cartridge; and
an actuation mechanism configured to slide the cassette with respect to the one or more track structures and to actuate the one or more alignment-locking features to either secure or release the disposable cartridge; and
said disposable cartridge including,
a housing having two or more alignment features; and
wherein the two or more alignment features are configured to receive an alignment-locking feature from the dialysis machine, wherein the alignment-locking feature is configured to pull the housing into the dialysis machine and secure the housing; and
a first, a second, and a third tubing lines mounted on the housing, wherein each tubing line comprises a U-shape section configured to fall into a recessed track of the dialysis machine.

2. The dialysis system of claim 1 wherein each of the two or more alignment features comprises a slot or a hole.

3. The dialysis system of claim 1 wherein the disposable cartridge's alignment-locking feature comprises a pin having actuatable side fingers.

4. The dialysis system of claim 3 said actuatable side fingers of the pin are configured to extend outward to grab onto the housing of the disposable cartridge when a pull-rod of the pin is pulled away from the housing.

5. The dialysis system of claim 3 said actuatable side fingers of the pin are configured to fold inward when a pull-rod of the pin is pushed forward toward the housing.

6. The dialysis system of claim 3 wherein said dialysis machine's actuation mechanism is configured to push the pin forward and retract the side fingers when it is set to a lock state.

7. The dialysis system of claim 3 wherein said dialysis machine's actuation mechanism is configured to pull the pin backward and expand the side fingers when it is set to an open state.

8. The dialysis system of claim 1 wherein said cassette's three tracks are recessed.

9. The dialysis system of claim 1 wherein said dialysis machine's actuation mechanism is configured to slide the cassette inward and push the three tubing lines against a roller when the actuation mechanism is set to a lock state.

10. The dialysis system of claim 1 wherein said dialysis machine's actuation mechanism is configured to slide the cassette outward to release pressure on the tubing lines when it is set to an open state.

11. The dialysis system of claim 1 wherein said dialysis machine's actuation mechanism comprises a linkage assembly configured to translate the cassette while the frame remains stationary and to actuate the one or more alignment-locking features to lock or release the disposable cartridge.

12. The dialysis system of claim 11 wherein said linkage assembly is configured to slide the cassette inward and push each tubing line against a pump motor when it is set to a lock state.

13. The dialysis system of claim 11 wherein said linkage assembly is configured to slide the cassette outward to release pressure on the tubing lines when it is set to an open state.

14. The dialysis system of claim 11 wherein said linkage assembly is configured to push the pin forward and retract the side fingers when it is set to a lock state.

15. The dialysis system of claim 11 wherein said linkage assembly is configured to pull the pin backward and expand the side fingers when it is set to an open state.

16. The dialysis system of claim 1 wherein said dialysis machine's actuation mechanism comprises:
a lever coupled to a first shaft,
a first cam coupled to the first shaft;
a plurality of linkages coupled to the first cam; and
a sliding element coupled to the plurality of linkages and to the cassette, and wherein the plurality of linkages are arranged such the cassette is slid inward or outward when the lever is actuated.

17. The dialysis system of claim 16 wherein said dialysis machine's actuation mechanism further comprises:
a gear assembly coupled to the first shaft;
a second shaft coupled to the gear assembly;
a second cam coupled to the second shaft; and
a pull-plate coupled to the second cam and to the pin, wherein the pull-plate and the pin are concurrently actuated forward or backward when the lever is actuated.

18. The dialysis system of claim 1 wherein said dialysis machine's actuation mechanism comprises:
a first set of one or more motors configured to slide the cassette with respect to the three track structures; and
a second set of one or more motors configured to actuate the one or more alignment-locking features to either secure or release the disposable cartridge.

* * * * *